US007048962B2

(12) United States Patent
Shekalim et al.

(10) Patent No.: US 7,048,962 B2
(45) Date of Patent: May 23, 2006

(54) STENT COATING DEVICE

(75) Inventors: Avraham Shekalim, Nesher (IL); Ascher Shmulewitz, Tel Aviv (IL)

(73) Assignee: LabCoat, Ltd., Galway (IE)

( * ) Notice: Subject to any disclaimer, the term of this patent is extended or adjusted under 35 U.S.C. 154(b) by 111 days.

(21) Appl. No.: 10/210,714

(22) Filed: Jul. 30, 2002

(65) Prior Publication Data

US 2003/0207019 A1 Nov. 6, 2003

Related U.S. Application Data

(63) Continuation-in-part of application No. 10/136,295, filed on May 2, 2002, now Pat. No. 6,645,547.

(51) Int. Cl.
*A61L 27/00* (2006.01)

(52) U.S. Cl. ..................... 427/2.24; 427/2.1; 427/2.25; 427/2.28; 427/2.3; 427/261; 427/424; 427/425

(58) Field of Classification Search ............... 427/2.24, 427/2.1, 2.25, 2.28, 2.3, 258, 261, 424, 425; 118/668, 669, 679, 680
See application file for complete search history.

(56) References Cited

U.S. PATENT DOCUMENTS 4,842,887 A 6/1989 Bolte
5,634,129 A 5/1997 Dickinson
5,640,587 A 6/1997 Davis et al.
5,649,139 A 7/1997 Weinreb et al.
5,652,884 A 7/1997 Palevich
5,706,517 A 1/1998 Dickinson
5,710,896 A 1/1998 Seidl
5,713,045 A 1/1998 Berdahl
5,717,877 A 2/1998 Orton et al.
5,729,671 A 3/1998 Peterson et al.

(Continued)

FOREIGN PATENT DOCUMENTS

WO WO 02/14078 A2 2/2002

OTHER PUBLICATIONS

"A Bit of Theory; What happens when a droplet hits a liquid surface? Why microdispensing needs highly dynamic systems. What makes the microdrop systems act as a pump?", www.microdrop.de/html/a bit of theory.html, Nov. 7, 2002, pp. 1-3.

(Continued)

*Primary Examiner*—Jennifer Michener
(74) *Attorney, Agent, or Firm*—Kudirka & Jobse, LLP

(57) ABSTRACT

The present invention is a method and device, which is suitable for use in an operating theater just prior to implantation, for selectively applying a medical coating to an implantable medical device, for example a stent. Disclosed is a device for use with a stent deployed on a catheter balloon. The device is configured to apply a medical coating of a desired thickness to the surface of a stent only. This is done by use of a drop-on-demand inkjet printing system in association with an optical scanning device. The device is further configured so as to, if necessary, apply a plurality of layered coats, each layered coat being of a different coating material, and if appropriate, different thickness. The section of the housing in which the stent is held during the coating procedure is detachable from the housing base. The detachable housing section may be easily cleaned and re-sterilized or simply disposed or simply disposed of.

21 Claims, 13 Drawing Sheets

U.S. PATENT DOCUMENTS

| | | | |
|---|---|---|---|
| 5,732,229 | A | 3/1998 | Dickinson |
| 5,734,852 | A | 3/1998 | Zias et al. |
| 5,737,559 | A | 4/1998 | Orton et al. |
| 5,752,245 | A | 5/1998 | Parrish et al. |
| 5,755,781 | A | 5/1998 | Jayaraman |
| 5,758,153 | A | 5/1998 | Atsatt et al. |
| 5,848,291 | A | 12/1998 | Milne et al. |
| 5,857,064 | A | 1/1999 | deSilva |
| 5,871,436 | A | 2/1999 | Eury |
| 5,877,768 | A | 3/1999 | Jain |
| 5,891,507 | A | 4/1999 | Jayaraman |
| 5,922,393 | A | 7/1999 | Jayaraman |
| 5,936,643 | A | 8/1999 | Tindell et al. |
| 5,972,027 | A | 10/1999 | Johnson |
| 6,001,311 | A | 12/1999 | Brennan |
| 6,042,600 | A | 3/2000 | Rosenthal et al. |
| 6,106,454 | A | 8/2000 | Berg et al. |
| 6,129,658 | A | 10/2000 | Delfino et al. |
| 6,169,550 | B1 | 1/2001 | Jain |
| 6,171,232 | B1 | 1/2001 | Papandreou et al. |
| 6,203,551 | B1 | 3/2001 | Wu |
| 6,214,115 | B1 | 4/2001 | Taylor et al. |
| 6,235,340 | B1 | 5/2001 | Lee et al. |
| 6,245,104 | B1 | 6/2001 | Alt |
| RE37,258 | E | 7/2001 | Patel et al. |
| 6,254,632 | B1 | 7/2001 | Wu et al. |
| 6,280,411 | B1 | 8/2001 | Lennox |
| 6,287,628 | B1 | 9/2001 | Hossainy et al. |
| 6,290,722 | B1 | 9/2001 | Wang |
| RE37,418 | E | 10/2001 | Tindell et al. |
| 6,306,166 | B1 | 10/2001 | Barry et al. |
| 6,309,380 | B1 | 10/2001 | Larson et al. |
| 6,312,406 | B1 | 11/2001 | Jayaraman |
| 6,315,792 | B1 | 11/2001 | Armstrong et al. |
| 6,335,029 | B1 | 1/2002 | Kamath et al. |
| 6,341,293 | B1 | 1/2002 | Hennessey |
| 6,341,907 | B1 | 1/2002 | Katsuyoshi |
| 6,368,658 | B1 | 4/2002 | Schwarz et al. |
| 6,395,326 | B1 * | 5/2002 | Castro et al. .............. 427/2.24 |
| 6,676,987 | B1 * | 1/2004 | Zhong et al. .............. 427/2.24 |

OTHER PUBLICATIONS

Cooley, Patrick et al., "Applications of Ink-Jet Printing Technology to BioMEMS and Microfluidic Systems," Proceedings, SPIE Conference on Microfluidics and BioMEMS, Oct. 2001, pp. 1-12.

"MicroDrop Microdosing System," MicroDrop Products, www.microdrop.de/html/microdropprod.html, Nov. 8, 2002, pp. 1-2.

"MicroDrop Dispenser Heads," MicroDrop Products, www.microdrop.de/html/dispenser heads.html, Nov. 8, 2002, pp. 1-2.

* cited by examiner

STENT COATING DEVICE

This is a continuation-in-part of U.S. patent application Ser. No. 10/136,295, filed on May 2, 2002, now U.S. Pat. No. 6,645,547.

FIELD OF THE INVENTION

The present invention relates to coating medical devices intended for in vivo deployment and, in particular, a method and device suitable for use in an operating theater just prior to implantation, for selectively applying a medical coating to an implantable medical device, for example a stent.

DEFINITIONS

The term "prosthesis" refers to any one of many medical coating applications including but not limited to coronary stents, peripheral vascular stents; abdominal aortic aneurysm (AAA) devices, biliary stents and catheters, TIPS catheters and stents, vena cava filters, vascular filters and distal support devices and emboli filter/entrapment aids, vascular grafts and stent grafts, gastro enteral tubes/stents, gastra enteral and vascular anastomotic devices, urinary catheters and stents, surgical and wound drainings, radioactive needles and other indwelling metal implants, bronchial tubes and stents, vascular coils, vascular protection devices, tissue and mechanical prosthetic heart valves and rings, arterial-venous shunts, AV access grafts, surgical tampons, dental implants, CSF shunts, pacemaker electrodes and leads, suture material, wound healing, tissue closure devices including wires, staplers, surgical clips etc., IUDs and associated pregnancy control devices, ocular implants, timponoplasty implants, hearing aids including cochlear implants, implantable pumps (like insulin pumps), implantable cameras and other diagnostic devices, drug delivery capsules, left ventricular assist devices (LVADs) and other implantable heart support and vascular systems, indwelling vascular access catheters and associated devices (like ports), maxilo fascial implants, orthopedic implants (joint replacement, trauma management and spine surgery devices), implantable devices for plastic and cosmetic surgery, implantable meshes (such as for hernia or for uro-vaginal repair, brain disorders, and gastrointestinal ailments).

The term "drop-on-demand" refers to any active or passive release of a predetermined drop or number of drops equivalent to a desired quantity of coating material. Drop-on-demand also refers to jetting when a sequence of drops is released. One example of "drop-on-demand" is the piezo drop-on-demand technology such as that manufactured by Ink Jet Technology, Inc. of San Jose, Calif. which provides applicators for a wide variety of coating applications. Such micro-machined ceramic designs are robust and chemically inert to almost every kind of fluid and coating and are compatible with a wide range of fluids with extreme pH values or strong solvent characteristics. Non-Newtonian fluids are also compatible with such devices due to the internal design of the applicator allowing laminar flow of the fluid. With a built in heater and high temperature operating potential, piezo drop-on-demand applicators are compatible with a wide variety of coating materials.

The term "detector" or "detecting" refers to any device or method which uses energy, such as magnetic, electrical, heat, light, etc. to determine whether a target at a desired location on the prosthesis has been located and signals the applicator to drop-on-demand or marks the location as one to be coated. The detector does not determine the location of the applicator relative to the target to provide feedback for positioning the applicator. The detector determines the points on the coordinate table for desired locations on the prosthesis by providing signals for the applicator controller that are immediately used or stored as coordinate tables. Examples of detectors are light sensitive devices such as CCD area cameras, CCD line cameras, high-resolution CMOS area cameras, or devices that can capture light reflected or transmitted by the prosthesis, and electrically sensitive devices such as capacitance detectors.

The term "applicator" or "applying" refers to any configuration, apparatus, or method for positioning a coating material to a surface from a reservoir such as a point source including but not limited to a nozzle, a dispenser, or tip, or a multipoint source. An example of an applicator is a drop-on-demand ink-jet.

The term "on-the-fly" refers to translation and drop-on-demand delivery that is synchronous or close to synchronous, and/or simultaneous or close to simultaneous. Unlike freestyle movement which requires stopping for validation of preceding and subsequent movement with relation to the prosthesis, on-the-fly continues to next movement without validation step. FIG. 13 illustrates an example of on-the-fly drop-on-demand with an embodiment where the axis of rotation 700 is stationery and applicator is moving in the Z axis. A servo controller 705 directs the Z drive 710 which is coupled to applicator 725 while monitoring the velocity and location of the applicator 725 via feedback device 715. The servo controller 705 keeps the Z drive 710 within predetermined limits of the required velocity and signals the applicator controller 720 to activate the drop-on-demand applicator using data from feedback device 715 with reference to coordinates from the pre-scan by a detector determining points to be coated. In this procedure the validation of the Z position of the applicator 725 is done in real-time by the servo controller 705. The servo controller 705 interacts with the axis of rotation to determine the next location based on the last location and the time which it takes Z drive 710 to move applicator 725 to the next location. Feedback device 715 provides feedback that is an internal servo-based logic procedure and is not connected to the actual location relative to the prosthesis and therefore does not become a validation step as discussed above. In alternative embodiments, the servo controller 705, Z drive 710, Z location feedback device 715, the applicator controller 720, and the applicator 725 can be all be bundled into the application control module (not shown).

The term "freestyle" refers to movement of an applicator over a portion of a prosthesis to be coated that requires validation through a predetermined user selected pattern and/or a feedback loop of applicator position relative to the portion of the prosthesis to be coated. Validation is done prior to delivery of the coating material. In one embodiment, freestyle movement moves the applicator over a predetermined position based on a user selected pattern. The position of the applicator is verified relative to the prosthesis and a new location is calculated. The applicator is moved to a new and more accurate location. The applicator delivers the coating material and then moves to the next predetermined location based on the user selected pattern.

It is noted that, as used in this specification and the appended claims, the singular forms "a," "an," and "the" include plural referents unless expressly and unequivocally limited to one referent. Thus for example, reference to "an applicator" includes two or more applicators, but "n is an integer from 1 to 60" means that n is one integer because that is limited to one integer. Also noted that as used herein, the term "polymer" is meant to refer to oligomers, homopolymers, and copolymers. The term "therapeutic agent" is meant to refer to drugs, therapeutic materials, diagnostic materials, inerts, active ingredients, and inactive ingredients.

For the purposes of this specification and appended claims, unless otherwise indicated, all numbers expressing quantities of ingredients or percentages or proportions of other materials, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

BACKGROUND OF THE INVENTION

The practice of coating implantable medical devices with a synthetic or biological active or inactive agent is known. Numerous processes have been proposed for the application of such a coating. Soaking or dipping the implantable device in a bath of liquid medication is suggested by U.S. Pat. No. 5,922,393 to Jayaraman, soaking in an agitated bath, U.S. Pat. No. 6,129,658 to Delfino et al. Devices introducing heat and/or ultrasonic energy in conjunction with the medicated bath are disclosed in U.S. Pat. Nos. 5,891,507 to Jayaraman and 6,245,4 BI to Alt. The device of U.S. Pat. No. 6,214,1 BI to Taylor et al. suggest spraying the medication by way of pressurized nozzles.

Initially such coating were applied at the time of manufacture. For various reasons such as the short shelf life of some drugs combined with the time span from manufacture to implantation and the possible decision of the medical staff involved concerning the specific drug and dosage to be used based on the patient's at the time of implantation, a need has arisen for technologies which permit applying a coating just prior to implantation. Wrapping the implantable device with medicated conformal film is disclosed in U.S. Pat. No. 6,309,380 BI to Larson et al. Dipping or soaking in a medicated bath just prior to implantation are suggested in U.S. Pat. Nos. 5,871,436 to Eury, 6,6,454 to Berg et al., and 6,1171,232 BI to Papandreou et al. U.S. Pat. No. 6,3,551 BI to Wu provides a bathing chamber for use with specific implantable device such as the stent deployed on the balloon of a catheter (FIG. 1).

Each of the methods and devices intended for use just prior to implantation, listed above, deposit the coating material onto any and all surfaces that are exposed to the coating. This may result in depositing coating material on surfaces on which the coating is unwanted or undesirable. Further, the coating may crack or break away when the implantable is removed from the implantation apparatus. An example of this would be a stent deployed on a catheter balloon. As the balloon is inflated and the stent is expanded into position, the coating may crack along the interface between the stent and the balloon. These cracks may lead to a breaking away of a portion of the coating from the stent itself. Similar problems can occur in cases where the coating technique fails to prevent inadvertent overlapping with the edges (e.g., internal surfaces along the edges) of various devices (e.g., struts of stents). This, in turn, may affect the medicinal effectiveness of the coating, and negatively affect the entire medical procedure.

It is known to use Ink-Jet technology to apply a liquid to selected portion of a surface. In the paper "Applications of Ink-Jet Printing Technology to BioMEMS and Microfluidic Systems," presented at the SPIC Conference on Microfluidics and BioMEMS, October, 01, the authors, Patrick Cooley, David Wallace, and Bogdan Antohe provide a fairly detailed description of Ink-Jet technology and the range of its medically related applications (http://www.microfab-.compapers/papers_pdf/spie biomems_O1_reprint.pdf).

A related device is disclosed in U.S. Pat. No. 6,001,311 to Brennan, which uses a moveable two-dimensional array of nozzles to deposit a plurality of different liquid reagents into receiving chambers. In the presentation of Cooley and the device of Brennan, the selective application of the material is based on an objective predetermined location of deposit rather that on a "subjective placement" as needed to meet the requirements of a specific application procedure. With regard to the application of coatings applied to medical devices with inkjet applicators, while it is possible to coat only a chosen portion of a device, such as only the stent mounted on a catheter, but not the catheter itself. This type of procedure using current technologies may, however, require providing complex data files, such as a CAD image of the device to be coated, and insuring that the device be installed in the coating apparatus in a precise manner so as to be oriented exactly the same as the CAD image.

Other systems which use ink-jet applicators apply the coating with a "freestyle" procedure. The freestyle points are determined by a preprogrammed user selected pattern that is unique to the particular shape or contour for the type of prosthesis and the desired coating to be achieved, much like a vector based printing approach. The ink-jet nozzle or prosthesis move in three-dimensionally with the aid of a motion control system. The motion control system enables the ink-jet nozzle to move over the portions of the prosthesis to be sprayed. Alternatively, a real-time picture can be taken with a camera to determine the position of the ink-jet nozzle in relation to the prosthesis. Based upon the feedback of nozzle location, the ink-jet applicator can be controlled by activating the spray, moving the ink-jet nozzle, and/or moving the prosthesis to adjust to the pattern to better conform with the actual prosthesis.

This type of system is particularly inefficient because the preprogrammed user selected pattern fails to accommodate inherent variability in the surface of the prosthesis. In one non-limiting embodiment, for example, a stent crimped around a balloon catheter will not be crimped such that it has the same surface each time. The crimping cannot be determined from the factory according to the manufacturer's specifications of the stent. Further, using this type of feedback loop serves merely as a "first impression" to control the spraying, nozzle position, and/or prosthesis position, and freestyle systems consequently increase the time required to apply the coating. In the operational theatre, this is undesired because many types of coatings (e.g., paclitaxel, rapamycin, or several other pharmaceutical compounds or bioactive agents) have to be applied to the stent crimped on the balloon catheter immediately prior to surgery.

The significance of delivering drug-loaded prostheses may offer savings benefit in time and cost. Studies have been conducted to show the importance of delivering the correct drug dose density on coronary stents to prevent restenosis by application of paclitaxel or rapamycin. Kandazari, David E. et al., *Highlights from American Heart Association Annual Scientific Sessions* 2001: Nov. 11 to 14, 2001, American Heart Journal 143 (2), 217–228, 2002; Hiatt, Bonnie L. et al., *Drug-Eluting Stents for Prevention of Restenosis: In Quest for the Holy Grail*, Catheterization and Cardiovascular Interventions 55:409–417, 2002; Kalinowski, M. et al., *Paclitaxel Inhibits Proliferation Of Cell Lines Responsible For Metal Stent Obstruction: Possible Topical Application In Malignant Bile Duct Obstructions*, Investigational Radiology 37(7):399–404, 2002. Other studies have shown how accuracy of dose related to cytotoxicity of coating drugs. Liebmann, J. E. et al., *Cytotoxic Studies Of Paclitaxel (Taxol) In Human Tumor Cell Lines*, Br. J. Cancer, 68(6): 1104–9, 1993; Adler, L. M. et al., *Analysis Of Exposure Times And Dose Escalation Of Paclitaxel In Ovarian Cancer Cell Lines*, Cancer, 74(7):1891–8, 1994; Regar, E. et al., *Stent Development And Local Drug Delivery*, Br. Med. Bulletin, 59:227–48, 2001. See also http://www.tctmd.com/expert-presentations: Farb, A., *Comparative Pathology Of Drug Eluting Stents: Insights Into Effectiveness And Toxicity From Animal Lab*, CRF Drug-Eluting Stent Symposium 2002; Grube, E., *Taxol-Eluting Stent Trials*, ISET 2002 Miami Beach, Mar. 19–23, 2002 (The effect of taxol on the edges of the stent and dose response screening); Carter, Andrew J., *Sirolimus: Pre-Clinical Studies—Evaluation Of Dosing, Efficacy And Toxicity*, TCT September 2001.

There is therefore a need for a device, and method for its use, whereby a coating is selectively applied to an implantable medical device just prior to implantation, such that only the device or selected portions thereof are coated. It would be desirable for the device to provide for user selection of coating material and dosage to be applied, thereby providing choices as to the specific coating material and dosage to be applied based on the specific needs of the patient at the time of implantation. It would be further desirable for the device to provide a sterile environment in which the coating is applied and the device is suitable for use in an operating theater.

Finally, a method and apparatus for coating a prosthesis is desired that will reduce the time of coating by coating the prosthesis "on the fly" without having to stop at each point to apply the coating.

SUMMARY OF THE INVENTION

The present invention is a method and device, which is suitable for use in an operating theater just prior to implantation, for selectively applying a medical coating to an implantable medical device, for example a stent.

According to the teachings of the present invention there is provided, a coating device for selectively applying a coating to surfaces of an object, the device applying the coating based upon optical properties of the surfaces such that the coating is applied to surfaces of a first type and is not applied to surfaces of a second type, the first type of surface being optically distinguishable from the second type of surface, the coating device comprising: at least one object-holding element configured to hold the object while a coating is applied; at least one optical scanning device deployed so as to scan at least a portion of the object, the optical scanning device configured so as to produce output indicative of the types of surfaces of the object; at least one coating applicator deployed so as to deposit a fluid so as to coat at least a portion of the object; at least one fluid delivery system in fluid communication so as to supply the fluid to the coating applicator; a processing unit being responsive at least to the output so as to selectively activate the coating applicator, thereby applying the coating substantially only to surfaces of the first type; and a drive system configured so as to provide relative motion between the surface of the object and the coating applicator, and between the surface of the object and the optical scanning device.

According to a further teaching of the present invention, the drive system is configured so as to rotate the object-holding element about an axis perpendicular to a direction of application of the coating applicator.

According to a further teaching of the present invention, the at least one object-holding element is implemented as two object-holding elements configured so as to simultaneously support the object at two different regions along a length of the object.

According to a further teaching of the present invention, the two object holding elements are mechanically linked so as to rotate synchronously about a single axis, the axis being perpendicular to a direction of application of the coating applicator.

According to a further teaching of the present invention, the at least one coating applicator includes a pressure-pulse actuated drop-ejection system with at least one nozzle.

According to a further teaching of the present invention, a spatial relationship between the coating applicator and the object is variable.

According to a further teaching of the present invention, the spatial relationship is varied along a first axis that is parallel to a direction of application of the coating applicator, and a second axis that is perpendicular to the direction of application of the coating applicator.

According to a further teaching of the present invention, the coating applicator is displaceable relative to the object-holding element, the displacement being along the first axis and the second axis, thereby varying the spatial relationship.

According to a further teaching of the present invention, both the coating applicator and the optical scanning device are deployed on a displaceable applicator base, displaceable relative to the object-holding element, the displacement being along the first axis and the second axis, thereby varying the spatial relationship.

According to a further teaching of the present invention, the at least one coating applicator is implemented as a plurality of coating applicators and the at least one fluid delivery system is implemented as an equal number of fluid delivery systems, each fluid delivery system supplying a different fluid coating material to the coating applicator with which the each fluid delivery system is in fluid communication.

According to a further teaching of the present invention, the object is a catheter that includes a balloon portion on which a stent is deployed, such that the stent is a surface of the first type and the balloon is a surface of the second type surface.

According to a further teaching of the present invention, the processing unit is responsive to an indication of the relative motion so as to change operational parameters of the coating device as required.

According to a further teaching of the present invention, the object-holding element, the coating applicator, the optical scanning device, the drive system and at least a portion of the fluid delivery system are deployed within a housing that includes an application compartment.

According to a further teaching of the present invention, the housing includes a base housing section and a detachable housing section.

According to a further teaching of the present invention, the application compartment is defined by portions of both the base housing section and the detachable housing section.

According to a further teaching of the present invention, the base housing section includes the coating applicator, at least a portion of the fluid delivery system, the optical scanning device and the processing unit and at least a first portion of the drive system, and the detachable housing section includes the object-holding element and at least a second portion of the drive system.

According to a further teaching of the present invention, the base housing section includes at least one fluid delivery system.

According to a further teaching of the present invention, the detachable housing section is disposable.

According to a further teaching of the present invention, the application compartment is a substantially sterile environment.

According to a further teaching of the present invention, the coating applicator, and the fluid delivery system are included in a removable sub housing, the removable subhousing being deployed with in the application compartment and the removable housing being detachably connected to the processing unit.

There is also provided according to the teachings of the present invention, a coating device for selectively applying a coating to surfaces of an object, the device applying the coating based upon optical properties of the surfaces such that the coating is applied to surfaces of a first type and is not applied to surfaces of a second type, the first type of surface being optically distinguishable from the second type of surface, the coating device comprising: a) a housing which includes an application compartment; b) at least one object holding element deployed within the application compartment, the object holding element configured to hold the object to which a coating is applied; c) a displaceable applicator base deployed within the application compartment, the applicator base including: i) at least one coating applicator aligned so as to deposit a fluid whereby at least a portion of the object is coated; and ii) at least one optical scanning device deployed so as to scan at least a portion of the object, the optical scanning device configured so as to produce scanning output indicative of the different types of surfaces of the object, the displacement of the applicator base resulting in a variance of a spatial relationship between the coating applicator base and the object; d) at least one fluid delivery system in fluid communication so as to supply the fluid to the coating applicator; e) a processing unit being responsive at least to the output so as to selectively activate the coating applicator, thereby applying the coating substantially only to surfaces of the first type; and f) a drive system configured so as to provide relative motion between the surface of the object and the applicator base.

According to a further teaching of the present invention, the housing includes a base housing section and a detachable housing section.

According to a further teaching of the present invention, the application compartment is defined by portions of both the base housing and the detachable housing section.

According to a further teaching of the present invention, the base housing section includes the displaceable applicator base, at least a portion of the fluid delivery system, and the processing unit, and at least a first portion of the drive system, and the detachable housing section includes the object holding element and at least a second portion of the drive system.

According to a further teaching of the present invention, the base housing section includes at least one fluid delivery system.

According to a further teaching of the present invention, the detachable housing section is disposable.

According to a further teaching of the present invention, the drive system is configured so as to rotate the object-holding element about an axis perpendicular to a direction of application of the coating applicator.

According to a further teaching of the present invention, the at least one object-holding element is implemented as two object-holding elements configured so as to simultaneously support the object at two different regions along a length of the object.

According to a further teaching of the present invention, the two object holding elements are mechanically linked so as to rotate synchronously about a single axis, the axis being perpendicular to a direction of application of the coating applicator.

According to a further teaching of the present invention, the at least one coating applicator includes a pressure-pulse actuated drop-ejection system with at least one nozzle.

According to a further teaching of the present invention, the at least one fluid delivery system is deployed in the base housing.

According to a further teaching of the present invention, the at least one coating applicator is implemented as a plurality of coating applicators and the at least one fluid delivery system is implemented as a like number of fluid delivery systems, each fluid delivery system supplying a different fluid coating material to the coating applicator with which the each fluid delivery system is in fluid communication.

According to a further teaching of the present invention, the coating applicator, and the fluid delivery system are included in a removable subhousing, the removable subhousing being detachably connected to the displaceable applicator base.

According to a further teaching of the present invention, the spatial relationship is varied along two axes, a first axis that is parallel to a direction of application of the coating applicator, and a second axis that is perpendicular to the direction of application of the coating applicator.

According to a further teaching of the present invention, the object is a catheter that includes a balloon portion on which a stent is deployed, such that the stent is a surface of the first type and the balloon is a surface of the second type.

According to a further teaching of the present invention, the processing unit is responsive to an indication of the relative motion so as to change operational parameters of the coating device as required.

There is also provided according to the teachings of the present invention, a coating method for selectively applying a coating to surfaces of an object, the method applying the coating based upon optical properties of the surfaces such that the coating is applied to surfaces of a first type and is not applied to surfaces of a second type, the first type of surface being optically distinguishable from the second type of surface, the coating device comprising: generating relative movement between the object and at least one optical scanning device and at least one coating applicator; optically scanning at least a portion of the object by use of the at least one optical scanning device so as to produce output indicative of the different types of surfaces of the object; responding to the output by selectively activating the coating applicator, thereby applying the coating substantially only to surfaces of the first type.

According to a further teaching of the present invention, the relative movement includes rotating the object about an axis perpendicular to a direction of application of the coating applicator.

According to a further teaching of the present invention, there is also provided simultaneously supporting the object at two different regions along a length of the object.

According to a further teaching of the present invention, the selective activation includes selectively activating a pressure-pulse actuated drop ejection system with at least one nozzle.

According to a further teaching of the present invention, the selective activation includes selectively activating a pressure-pulse actuated drop ejection system with at least one nozzle that is included in a removable sub housing, the removable sub-housing further including a fluid delivery system in fluid communication so as to supply coating material to the coating applicator.

According to a further teaching of the present invention, the applying is preformed by selectively activating one of a plurality of coating applicators, wherein the at least one coating applicator implemented as the plurality of coating applicators, each of the plurality of coating applicators applying a different coating.

According to a further teaching of the present invention, the applying is preformed by selectively activating, in sequence, the plurality of coating applicators, thereby applying a plurality of layered coats, each one of the plurality of layered coats being of a coating material that is different from adjacent layered coats.

According to a further teaching of the present invention, responding to the output includes the output being indicative of a balloon portion of catheter and a stent deployed on the balloon, such that the stent is a surface of the first type and the balloon is a surface of the second type.

According to a further teaching of the present invention, responding to the output includes the output being indicative only of a surface of the first type thereby applying the coating to substantially the entire surface of the object.

According to a further teaching of the present invention, there is also provided varying a spatial relationship between the coating applicator and the object.

According to a further teaching of the present invention, the varying is along two axes, a first axis that is parallel to a direction of application of the coating applicator, and a second axis that is perpendicular to the direction of application of the coating applicator.

According to a further teaching of the present invention, the varying is accomplished by displacing the coating applicator.

According to a further teaching of the present invention, the varying is accomplished by varying the spatial relationship between the object and a displaceable applicator base upon which the at least one coating applicator and the at least one optical scanning device are deployed.

According to a further teaching of the present invention, controlling the varying is accomplished by the processing unit.

According to a further teaching of the present invention, there is also provided responding to an indication of the relative motion so as to change operational parameters of the coating device as required.

According to a further teaching of the present invention, generating relative movement, the optically scanning at least a portion of the object, and the selectively activating the coating are preformed within a housing.

According to a further teaching of the present invention, there are multiple applicators provided for coating injection to achieve better performance.

According to a further teaching of the present invention, there is a cleaning material container provided to clean the applicator at the end of the application process. The cleaning material is compatible with the drug being used.

According to a further teaching of the present invention, there is a cover provided on the front surface of the applicator at the end of the use.

According to a further teaching of the present invention, a wiper is provided to clean the applicator surface.

According to a further teaching of the present invention, a metering gauge is provided to measure the quantity of coating material applied through the applicator.

According to a further teaching of the present invention, optical scanning is provided by the use of a light source that can scan intensity in white, black or other colors.

According to a further teaching of the present invention, other application, dispensing, and depositing methods can be used with the features of the present invention.

According to a further teaching of the present invention, a method for coating comprises (a) providing a prosthesis having identifiable features; (b) pre-scanning the prosthesis prior to coating to identify the features and to obtain coating coordinates for the features; and (c) depositing a coating material at desired regions of the prosthesis as a function of the coordinates.

According to a further teaching of the present invention, the method comprises (d) determining paths between the coating coordinates for an applicator to deposit the coating material.

According to a further teaching of the present invention, the method comprises (e) determining a sequence for the coating coordinates.

According to a further teaching of the present invention, the method comprises (f) determining vectors between the coating coordinates in the sequence.

According to a further teaching of the present invention, the method comprises (d) determining a predetermined path independent of the coating coordinates.

According to a further teaching of the present invention, the predetermined path covers a surface area of the prosthesis, wherein the surface area comprises the coating coordinates.

According to a further teaching of the present invention, the predetermined path is a function of the overall contour or geometric shape of the prosthesis.

According to a further teaching of the present invention, the method comprises (d) post-scanning the prosthesis after coating.

According to a further teaching of the present invention, the post-scanning comprises rotating the prosthesis and detecting of the coated prosthesis.

According to a further teaching of the present invention, the pre-scanning comprises rotating the prosthesis and detecting of the prosthesis.

According to a further teaching of the present invention, detecting comprises detecting energy from the identifiable features of the prosthesis.

According to a further teaching of the present invention, the pre-scanning comprises analyzing the images for edges associated with the prosthesis.

According to a further teaching of the present invention, the pre-scanning comprises determining the coating coordinates from the edges.

According to a further teaching of the present invention, detecting comprises capturing energy transmitted around identifiable features of the prosthesis.

According to a further teaching of the present invention, pre-scanning comprises analyzing images for the edges associated with the prosthesis.

According to a further teaching of the present invention, pre-scanning comprises determining the coating coordinates from the edges.

According to a further teaching of the present invention, the coating material is chosen from polymers, therapeutic agents, and mixtures thereof.

According to a further teaching of the present invention, the method for coating comprises (a) providing a prosthesis; (b) pre-scanning the prosthesis prior to coating to obtain coating coordinates for the prosthesis; (c) coating the prosthesis at the coating coordinates; and (d) post-scanning the prosthesis after coating.

According to a further teaching of the present invention, the coating comprises translating the coating applicator and drop-on-demand delivery of a quantity of coating from a coating applicator, wherein said translating and said delivery are on-the-fly.

According to a further teaching of the present invention, the coating process comprises raster type coating step.

According to a further teaching of the present invention, the coating process comprises vector type coating step.

According to a further teaching of the present invention, pre-scanning comprises rotating the prosthesis and detecting of the prosthesis.

According to a further teaching of the present invention, pre-scanning comprises rotating a detector and detecting of the prosthesis.

According to a further teaching of the present invention, post-scanning comprises rotating the prosthesis and detecting of the coated prosthesis.

According to a further teaching of the present invention, post-scanning comprises rotating a detector and detecting of the coated prosthesis.

According to a further teaching of the present invention, detecting comprises capturing energy from the prosthesis or capturing energy transmitted around the prosthesis.

According to a further teaching of the present invention, pre-scanning and the post-scanning comprises analyzing the images for edges of the prosthesis.

According to a further teaching of the present invention, pre-scanning comprises determining the coating coordinates from the edges.

According to a further teaching of the present invention, the analyzing comprises comparing images from the pre-scanning and the post-scanning.

According to a further teaching of the present invention, analyzing comprises identifying coating errors.

According to a further teaching of the present invention, the method comprising repeating the coating step to re-coat the prosthesis at coordinates associated with detected coating errors.

According to a further teaching of the present invention, the method comprises assigning a coating quality approval to the coated prosthesis.

According to a further teaching of the present invention, analyzing comprises optically distinguishing a first type of surface from a second type of surface.

According to a further teaching of the present invention, analyzing comprises rendering a three-dimensional shape from the images.

According to a further teaching of the present invention, analyzing comprises identifying pigment in a coating applied to the prosthesis.

According to a further teaching of the present invention, coating comprises jetting with hot air, wherein the hot air evaporates a volatile solvent in a coating material.

According to a further teaching of the present invention, coating comprises directing infrared radiation, wherein the infrared radiation evaporates a volatile solvent in a coating material.

According to a further teaching of the present invention, the coating material is chosen from polymers, therapeutic agents, and mixtures thereof.

According to a further teaching of the present invention, the method for coating comprises (a) providing a prosthesis having identifiable features; (b) determining a predetermined path independent of the features; and (c) coating the prosthesis at desired regions, wherein said regions are a function of the features.

According to a further teaching of the present invention, the predetermined path covers a surface area of the prosthesis, wherein the surface area comprises the desired regions.

According to a further teaching of the present invention, the predetermined path is a function of the overall contour or geometric shape of the prosthesis.

According to a further teaching of the present invention, the coating process comprises a raster type coating step.

According to a further teaching of the present invention, the coating material is chosen from polymers, therapeutic agents, and mixtures thereof.

According to a further teaching of the present invention, the apparatus for coating comprises an applicator for applying a coating material to a prosthesis; a detector for scanning the prosthesis; and an applicator controller connected to the detector and the applicator, wherein the applicator controller is adapted to on-the-fly coating.

According to a further teaching of the present invention, the prosthesis comprises identifiable features for which the detector provides coating coordinates for the applicator controller.

According to a further teaching of the present invention, the applicator controller is adapted to determine paths between the coating coordinates for the applicator.

According to a further teaching of the present invention, the system for coating comprises (a) means for providing a prosthesis having identifiable features; (b) means for pre-scanning the prosthesis prior to coating to identify the features and to obtain coating coordinates for the features; and (c) means for applying a coating material at desired regions of the prosthesis as a function of the coordinates.

According to a further teaching of the present invention, the system comprising (d) means for determining paths between the coating coordinates for an applicator.

According to a further teaching of the present invention, the system comprising (e) means for determining a sequence for the coating coordinates.

According to a further teaching of the present invention, the system comprising (f) means for determining vectors between the coating coordinates in the sequence.

According to a further teaching of the present invention, the system comprising (d) means for determining a predetermined path independent of the coating coordinates.

According to a further teaching of the present invention, a computer program product for coating comprises computer-readable media having computer-readable code, the computer program product comprising the following computer-readable program code for effecting actions in a computing platform (a) program code for providing a prosthesis having identifiable features; (b) program code for prescanning the prosthesis prior to coating to identify the features and to obtain coating coordinates for the features; and (c) program code for depositing a coating material at desired regions of the prosthesis as a function of the coordinates.

According to a further teaching of the present invention, the computer program comprises (d) program code for determining paths between the coating coordinates for an applicator.

According to a further teaching of the present invention, the computer program comprises (e) program code for determining a sequence for the coating coordinates.

According to a further teaching of the present invention, the computer comprises (f) program code for determining vectors between the coating coordinates in the sequence.

According to a further teaching of the present invention, the computer program product comprising (d) program code for determining a predetermined path independent of the coating coordinates.

According to a further teaching of the present invention, the applicator control module comprises an applicator adapted to drop-on-demand a quantity of coating material at a desired location of a prosthesis; and an applicator controller adapted to on-the-fly coating.

According to a further teaching of the present invention, the applicator controller comprises of a servo controller, a driver for said applicator, and a location feedback device.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and device, which is suitable for use in an operating theater just prior to implantation, for selectively applying a medical coating to an implantable medical device, for example a stent.

The principles and operation of a coating device according to the present invention may be better understood with reference to the drawings and the accompanying description.

By way of introduction, the embodiment discussed herein is a device for applying a medical coating to a stent deployed on a catheter, the coating being applied just prior to implantation and if desired in the operating theater. The use of optical scanning devices enables a processing unit to distinguish between the surface area of the stent and the surface area of the catheter. The processing unit selectively activates the coating applicator so as to apply the coating to substantially only the stent and not the balloon or other portion of the catheter. The coating applicator discussed herein is, by non-limiting example, a pressure-pulse actuated drop-ejection system with at least one nozzle. A readily available pressure-pulse actuated drop-ejection system, which is well suited for the present invention, is a drop-on-demand inkjet system. It should be noted, however, that any coating application system that may be selectively activated is within the intentions of the present invention. While the discussion herein is specific to this embodiment, which is intended for use in an operating theater, among other places, this embodiment is intended as a non-limiting example of the principles of the present invention. It will be readily apparent to one skilled in the art, the range of applications suited to the principals of the present invention. Even the device described herein, as a non-limiting example, with minor adaptations to the object-holding element and choice of fluid coating materials, is well suited for a wide range of objects to which a coating is applied.

Figure 1:
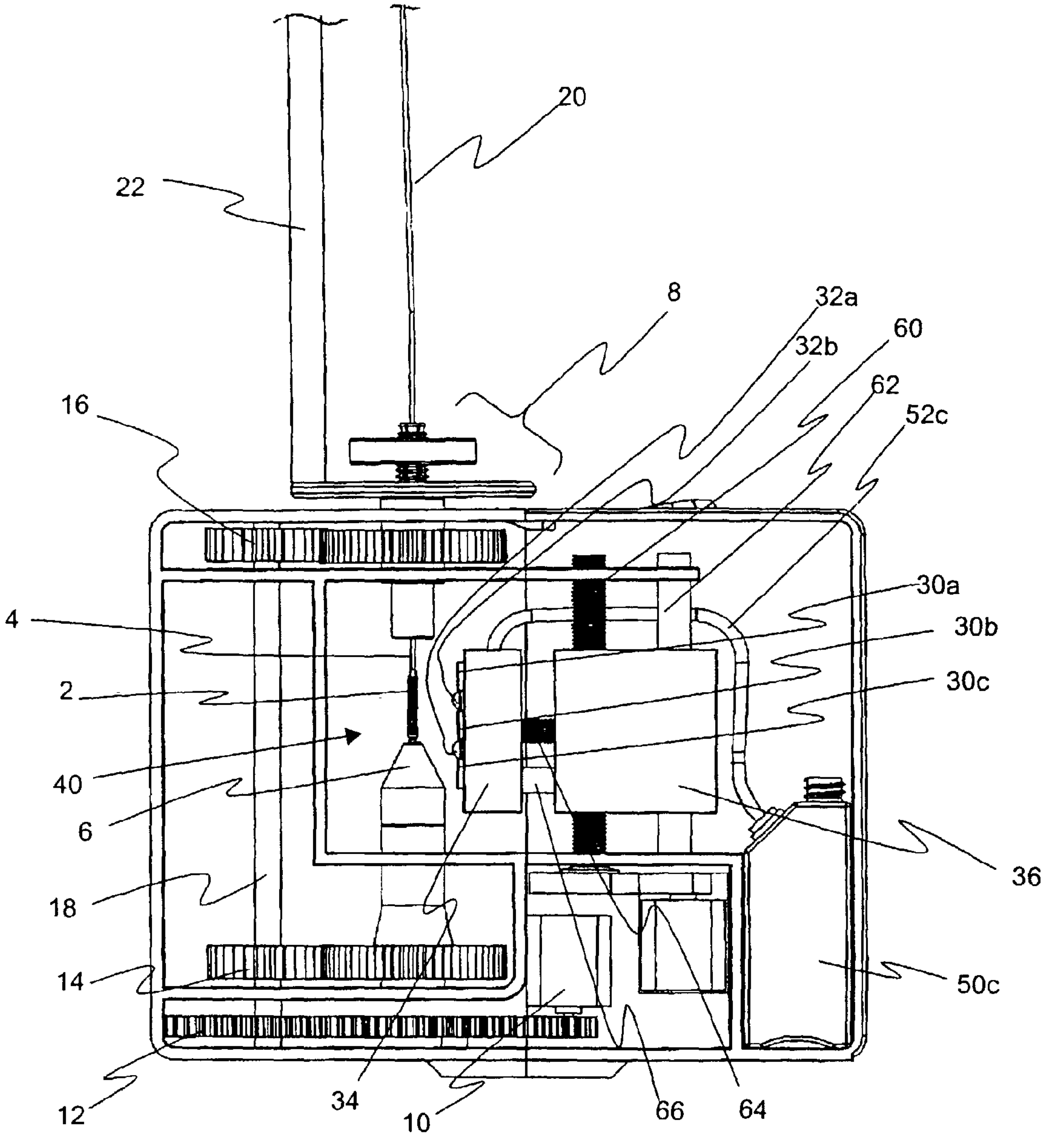
FIG. 1 is a cut-away side elevation of a stent coating device constructed and operative according to the teachings of the present invention.
Figure 2:
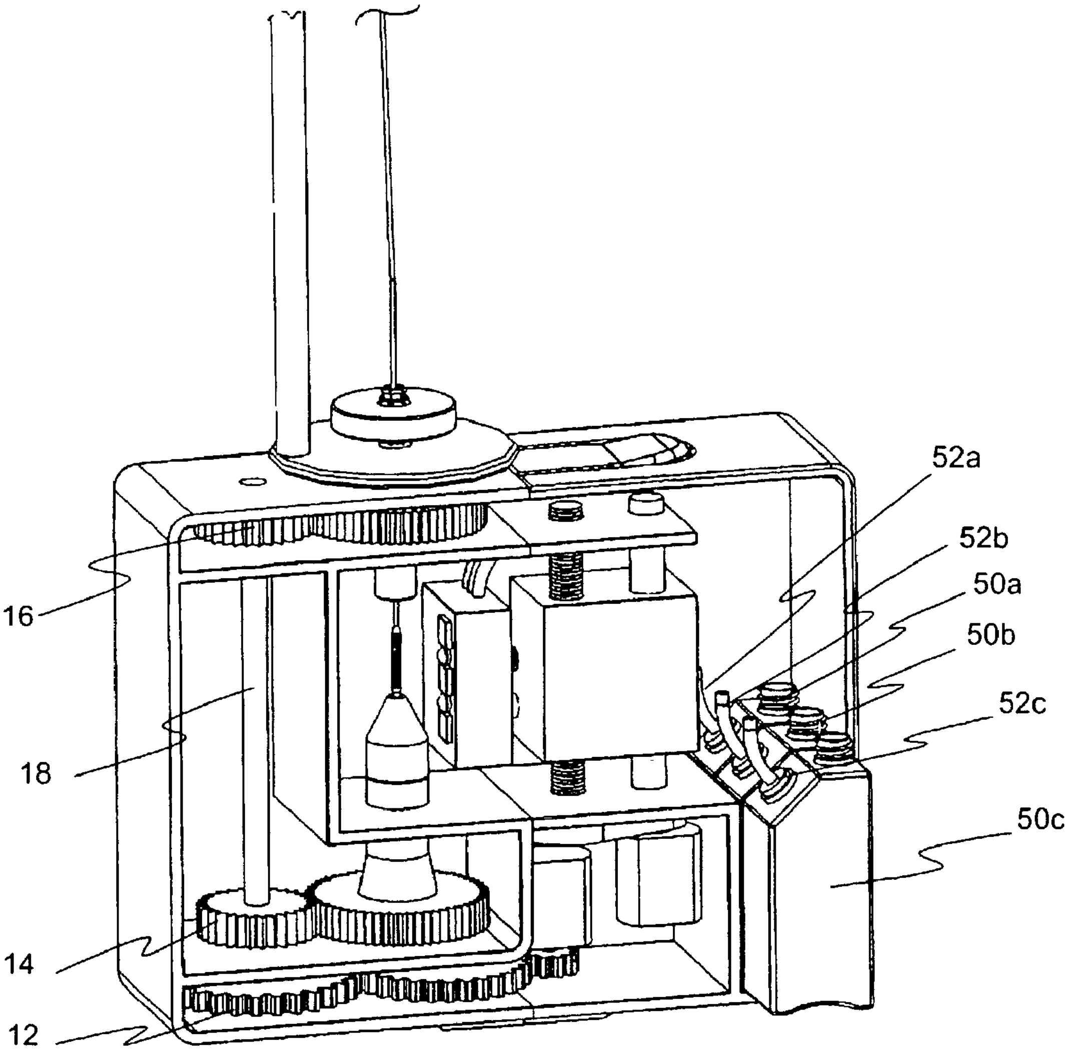
FIG. 2 is a cut-away perspective view of the stent coating device of FIG. 1.
Figure 6:
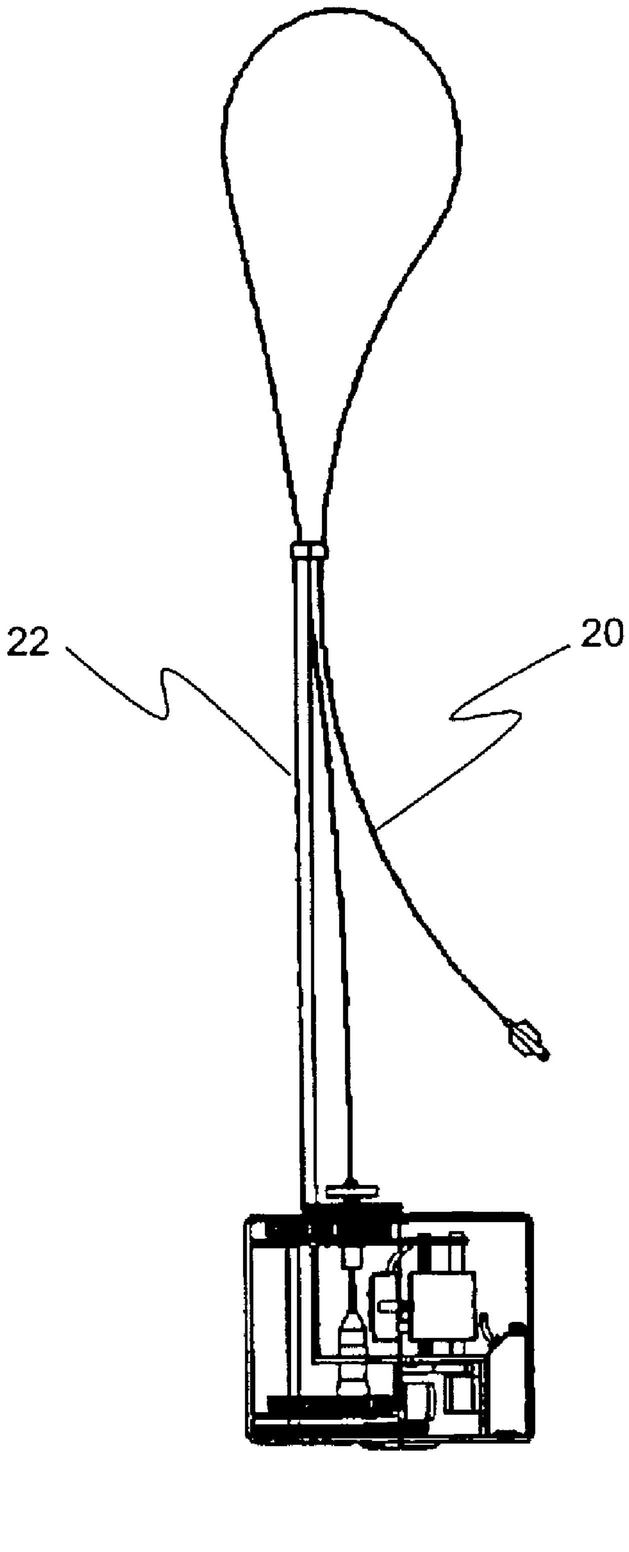
FIG. 6 is a side elevation of the stent coating device of FIG. 1 showing the full length of a catheter being supported by the support antenna.

Referring now to the drawings, as mentioned above, FIG. 1 illustrates a device for applying a coating to a stent 2 that is deployed on a catheter 4 . The coating being applied may be a synthetic or biological, active or inactive agent. The perspective view of FIG. 2 is of the same side of the device as FIG. 1, and therefore when the description of elements of the device will be better understood, FIG. 2 will be referenced. The catheter 4 is placed in an application compartment 40 and held in position by a rotatable catheter-holding base 6 and a rotatable upper catheter-holding element 8 , which are configured for substantially continued rotation, that is they may complete a plurality of full 360 degree rotations, as required, during the coating process. The actual rotation may be substantially fully continuous (non-stop) or intermittent. The upper catheter-holding element will be discussed in detail below with regard to FIG. 4. The enclosed application compartment provides a sterile environment in which the coating process is performed. The rotation of the catheter-holding base and the upper catheter-holding element is actuated and synchronized by a motor and gear system that includes gear clusters 12,14,16 , and shaft 18 (see also FIG. 2). Alternatively, the gears may be replaced by drive belts or drive chains. The remaining length of the catheter is supported by a support antenna 22 , as illustrated, by non-limiting example, in FIG. 6. As noted above, the object-holding elements may be modified so as to hold any object suitable for coating according to the teachings of the present invention.

The coating is applied by a drop-on-demand inkjet system in association with an optical scanning device and processing unit. As the object is rotated by the object-holding element, the optical scanning device scans the surface of the object. The out-put from the scanning device is used by the processing unit to determine if the surface area currently aligned with the coating applicator is of the type of surface to be coated. When it is determined that the desired type of surface is aligned with the coating applicator, the processing unit activates the coating applicator and the coating is dispensed. The embodiment shown here includes three inkjet coating applicators 30*a*, 30*b*, and 30*c*, and two optical scanning devices 32*a* and 32*b*. The optical scanning devices may be configured to generate digital output or an analog signal, which is in turn analyzed by the processing unit. It should be noted that the number of coating applicators and scanning devices may be varied to meet design or application requirements. The three coating applicators and the two optical scanning devices are mounted on a displaceable applicator head 34 . The position of the applicator head within the application compartment, and thereby the spatial relationship between the coating applicator and the stent, or other object being coated, is regulated by the application control module 36 , which is, in turn, controlled by the processing unit. The change of position of the applicator head is effected vertically by turning the vertical positioning screw 60 in conjunction with guide shaft 62 , and effected horizontally by turning the horizontal positioning screw 64 in conjunction with guide shaft 66 . The vertical repositioning in conjunction with the rotation of the object enables the coating applicator to traverse substantially the entire surface of the object requiring coating.

Fluid coating material is stored in three fluid reservoirs 50*a*, 50*b*, and 50*c* (see FIG. 2 ), and supplied to the respective coating applicators by the fluid supply hoses 52*a*, 52*b* and 52*c* (see FIG. 2). In general use, each of the fluid reservoirs contains a different coating material, thus, each coating applicator will deposit a different coating material on the stent or other objected being coated, as required. Further, a plurality of coats may be applied, each coat being of a different coating material and, if required, of a different thickness. Thus, at the time of coating, a single appropriate coating material may be chosen from the materials provided, or a combination of coatings may be chosen. It should be noted that while the fluid reservoirs are shown here in a compartment inside the device housing, this need not always be the case, and the reservoirs may be external to the housing.

Figure 3:
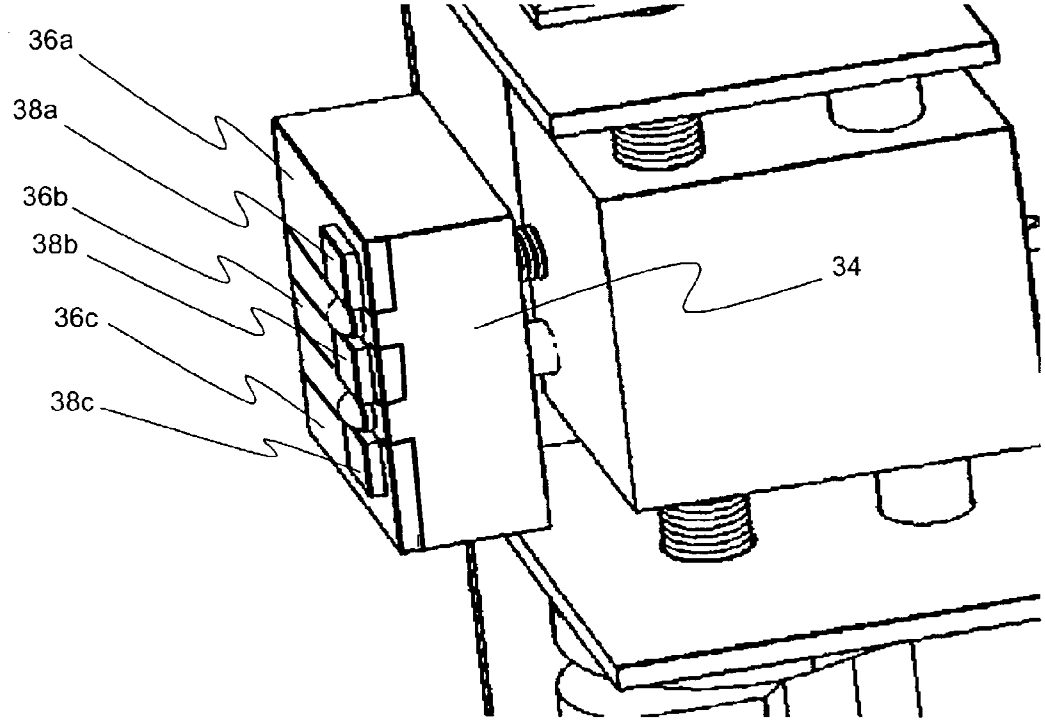
FIG. 3 is a perspective detail of an alternative displaceable applicator head constructed and operative according to the teachings of the present invention, shown here configure with disposable coating applicators.

It should be noted that, alternatively, the inkjet system may be deployed in a disposable housing that also includes a fluid reservoir filled with coating material. The fluid reservoir may be an enclosed volume that is integral to the disposable housing or it may be a coating filled cartridge that is inserted into a receiving cavity in the disposable housing. In this case, as illustrated in FIG. 3, the displaceable applicator head 34 is configured so as to accept one or more of the disposable housings 36*a*, 36*b*, and 36*c*, which in turn house inkjet coating applicators 38*a*, 38*b*, and 38*e* respectively. The fluid reservoirs (not shown) for each applicator are housed in that portion of the disposable housing that is deployed within the displaceable applicator head 34.

Figure 4:
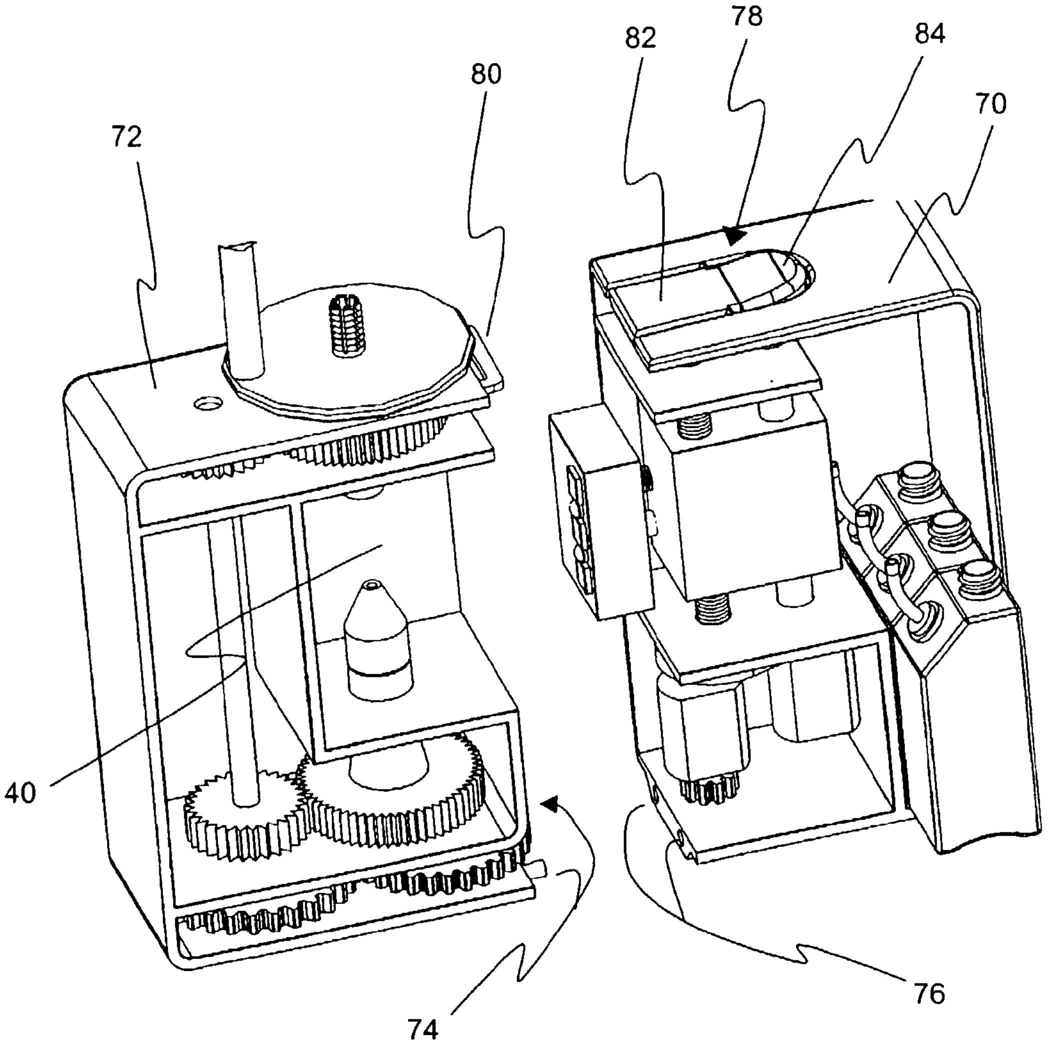
FIG. 4 is a cut-away perspective view of the stent coating device of FIG. 1, showing the detachable section of the housing separated from the base section of the housing.

FIG. 4 illustrates how the base housing section 70 and the detachable housing section 72 are interconnected. The two sections are held together by inserting pins 74, extending from the detachable housing section, into the corresponding holes 76, located in the base housing section, and engaging the latch mechanism 78 with the catch element 80. Detachment of the two sections is accomplished by pressing the release "button" 84, which raises the end 82 of the latch thereby releasing the catch element. The two sections are then pulled apart. As seen here more clearly, the application compartment is defined by a top, floor and three walls located in the detachable housing section and one wall on the base housing section. The detachable housing section is configured so as to be disposable, or if desired, easily cleaned and re-sterilized.

Figure 5:
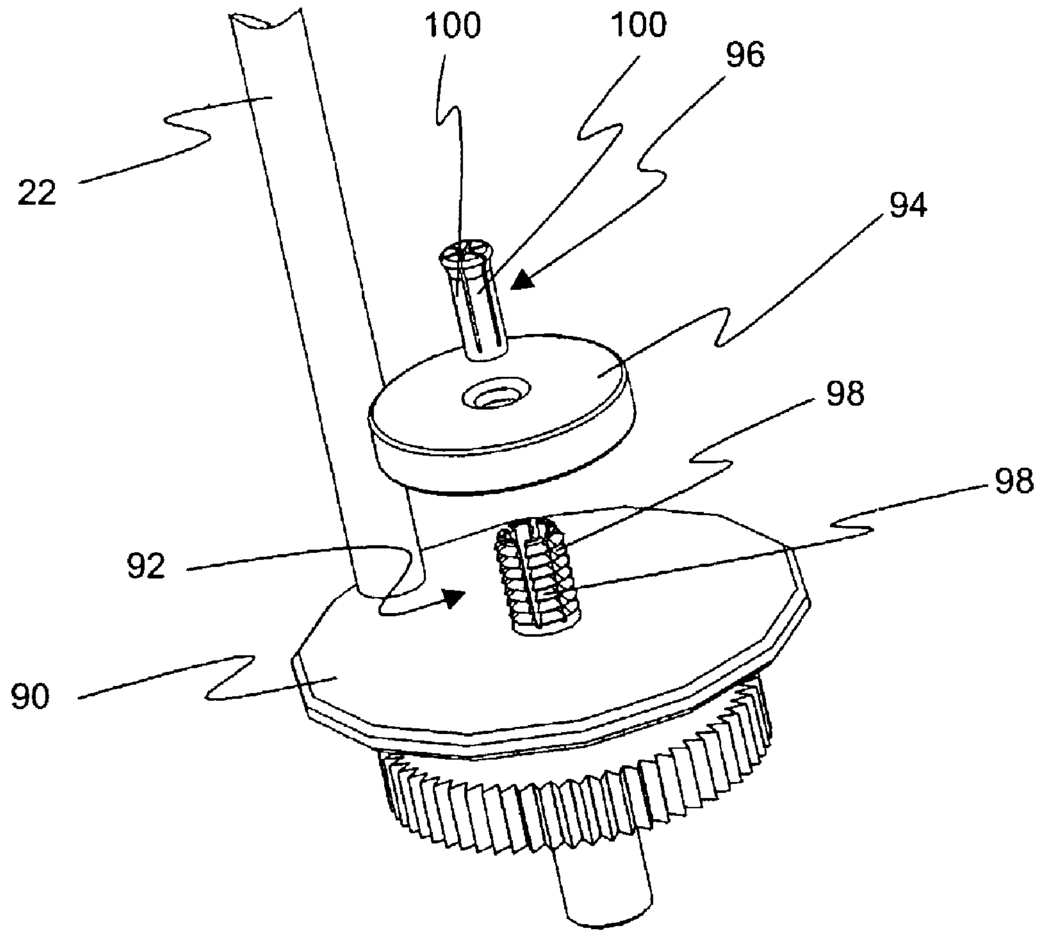
FIG. 5 is a perspective detail of an upper stent holding element, constructed and operative according to the teachings of the present invention.

The detail of FIG. 5 shows the components of the upper catheter-holding element. Extending from substantially the center of the rotating base plate 90 , is a threaded tube 92 . This tube is the external end of the passageway through which the catheter tip with the stent attached is inserted in order to deploy the stent in the application compartment of the coating device. The tube is cut longitudinally several times, to create threaded sections 98 , here six, that are configured so as to flex outward from the center. The tightening-disk 94 , has a correspondingly threaded center hole for deployment on the tube 92 such that when the tightening-disk is brought to a position proximal to the base plate, the threaded sections near the end of the tube will flex outwardly thereby enlarging the diameter of the opening. The gripping element 96 also has divergently flexing "fingers" 100 . In operation, the gripping element 96 is deployed around the catheter, which is then passed through the tube and into the application compartment. Once the catheter is positioned on the catheter holding base, the gripping element is at least partially inserted into the opening of the tube. The tightening-disk 94 is then rotated about the tube, and thereby brought to a position proximal to the end of the tube, the outwardly flexing sections of the tube 98 are brought into an un-flexed state thereby decreasing the diameter of the opening. The decrease in the diameter of the tube opening pushes the "fingers" of the gripping element against the catheter, thereby holding the catheter in place.

A non-limiting example of the stent coating process as accomplished by the above describe device would be as follows:

1. The fluid reservoirs are filled with the required fluid coating materials.

2. The parameters of the coating are inputted into the processing unit. The parameters may include, by non-limiting example, the coating material to be applied, the thickness of the coating, number of multiple layers of different coating material, the order in which the layered materials are to be applied, and the thickness of each layer. The parameters may be determined by the physician at the time the coating is applied or the parameters may be pre-set, such as those determined by medical regulations. In the case of pre-set parameters, the physician would simply input a "start" command.

3. The catheter is positioned in the application compartment and the upper catheter-holding element is tightened.

4. As the catheter rotates, the optical scanning device scans the surface of the catheter, to distinguish between the surface of the balloon and the surface of the stent.

5. When a portion of the surface of the stent is detected and determined to be in alignment with the appropriate coating applicator, the processing unit selectively activates the applicator, thereby ejecting the necessary amount of coating material, which is deposited substantially only on the surface of the stent.

6. Throughout the coating process, the position of the applicator head is adjusted as required. This adjustment may bring the coating applicator closer to, or farther away from, the surface of the stent, and it may adjust the vertical deployment of the coating applicator, thereby allowing different areas of the surface of the stent to be coated. Further, if a different fluid coating material is needed for a different layer of the coating, the coating applicator for that particular coating material may be brought into appropriate alignment for deposition of the new coating material on the stent.

7. When the coating process is completed, the catheter with the now coated stent is removed from the device, and the stent is ready for implantation.

8. The detachable housing section is removed and may be cleaned and sterilized for re-use, or simply discarded.

It should be noted that in some cases it may be desirable to coat substantially the entire surface of the object being coated. This may be accomplished in at least two ways. The object itself may have only one type of surface. Alternatively, the scanning device may be configured so as to provide adjustable scanning sensitivity. In such a case, the sensitivity of the scanning device may be adjusted such that the out-put is indicative of only one type of surface and the processing unit is unable to distinguish between different types of surfaces.

Figure 7A:
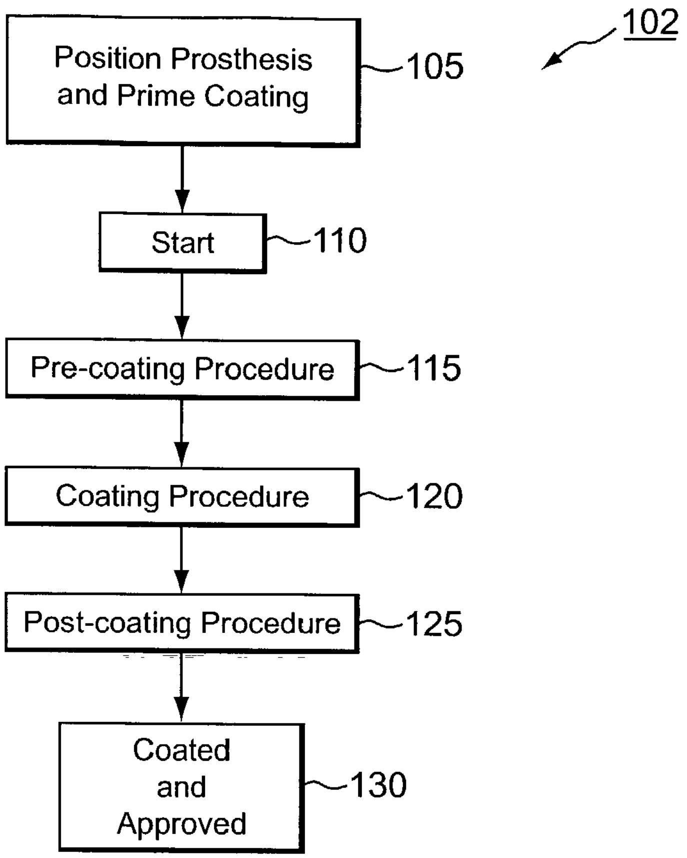
FIG. 7A is a flow chart of a non-limiting embodiment of a method for coating a stent according to the present invention.
Figure 7B:
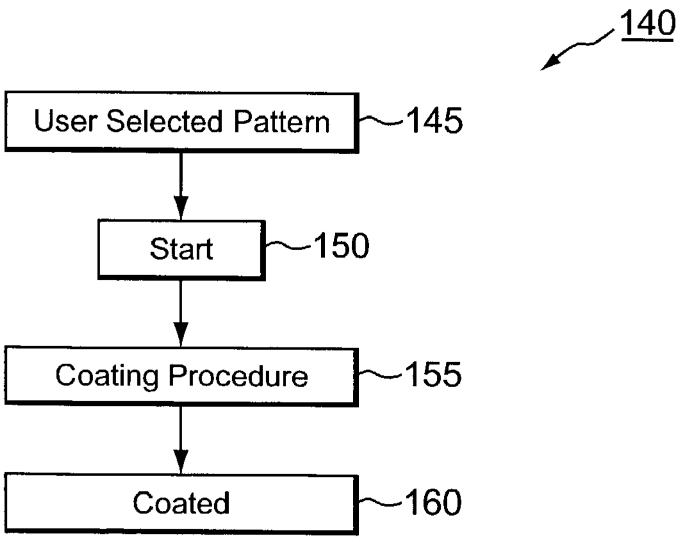
FIG. 7B is a flow chart of the method known in the art for coating a stent.

The flowchart of FIG. 7A illustrates a process for coating a prosthesis 102 based on the present invention. In this non-limiting example, the prosthesis is a stent that is to be coated with a therapeutic agent. The first step 105 is to place the stent and therapeutic agent container in the stent coating device. The system is then ready for processing the stent. The system starts at 110 . The pre-coating procedure 115 collects information in the processing unit (not shown) of the stent coating device to be used during the coating procedure 120 . The post-coating procedure 125 verifies that the stent has been properly coated and should be approved for removal 130 . The flowchart of FIG. 7B illustrates the process for coating stents 140 known in the art. The user selects a pattern 145 according to the type of stent to be coated and the pattern of coating to be delivered. The pattern selected varies on parameters provided by the stent manufacturer and the coating to be applied. The process starts 150 according to the pattern that has been selected. The coating procedure 155 applies the coating to the stent, and once complete 160 the coated stent 140 is ready for removal.

Figure 8:
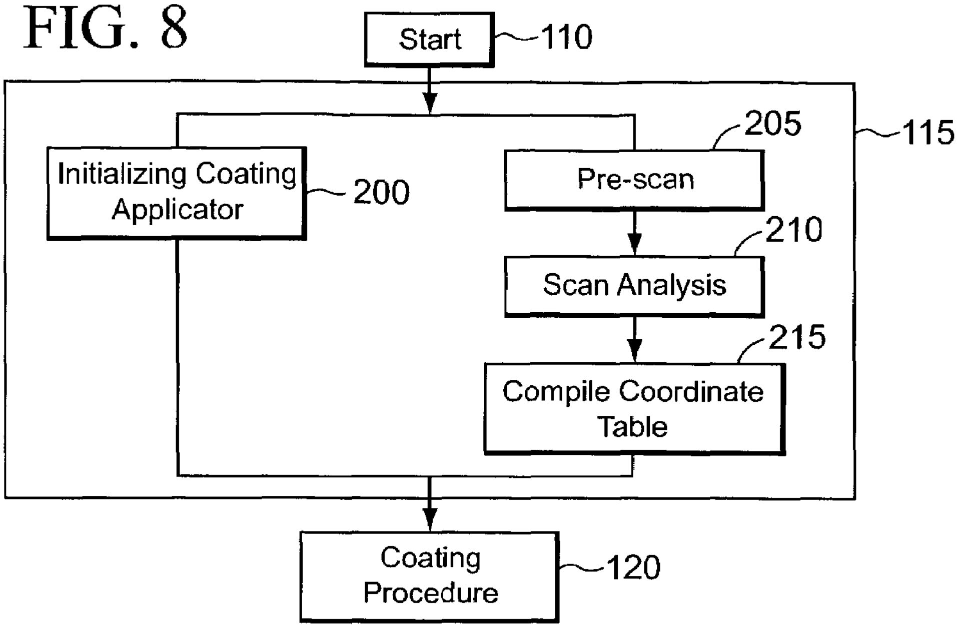
FIG. 8 is a flow chart of a non-limiting embodiment of the pre-coating procedure according to the present invention.

FIG. 8 illustrates the pre-scanning procedure 115. The stent is pre-scanned 205 prior to the coating procedure 120. In parallel, the application control module is initialized 200. Initialization of the application control module comprises finding a specific point on the stent to begin coating. The pre-scan is analyzed 210 in the processing unit. The analysis determines and compiles the coating coordinates table 215 to be used to position the application control module.

There is a large standard deviation between stents of the same design, especially after the stent is crimped on the balloon catheter. The preprogrammed pattern is not helpful to manage these deviations from the design. Pre-scanning can provide a check for defects in the stent structure prior to coating. Pre-scanning can also provide the best positions on to which to spray the coating. Crimping does not always result in a uniform deformation of the stent structure. Some portions of the stent may be more densely packed than other portions. Some intersections of stent struts may have different angles of incidence. Pre-scanning can provide the optimal path to follow over the stent surface to be coated. Some applications require only a portion of the stent to be coated. Pre-scanning can prevent over-jetting of the coating on a specific location. Over-jetting can result in inadvertent coating from the stent on the balloon catheter.

Scanning can be achieved by a variety of imaging techniques known in the art of imaging, including but not limited to photographic, video, infrared, and VCSEL (Vertical Cavity Surface Emitting Laser) technologies using a variety of detectors. VCSELs can be used as the detector for optical imaging, and can double as the applicator itself. Choquette, Kent D., *Vertical Cavity Surface Emitting Lasers—Light for Information Age*, MRS Bulletin, pp. 507–511, July 2002. In one non-limiting embodiment, a photograph of the stent is taken by a detector. The stent is rotated slightly (e.g., one-half to a few degrees) and then another photograph is taken, resulting in at least several dozen photographs total. The detector is focused sufficiently close to the stent to record enough resolution relative to the coating droplet to be applied. If the stent is long, the rotation may have to be repeated to capture the top and bottom of the stent.

A light source can be positioned on the same side as the detector or on the opposite side of the detector relative to the stent. In the embodiment where the light source is on the same side as the detector, the detector receives light reflected by the stent. The stent appears light in color and the balloon appears dark in color. In the embodiment where the light source is on the opposite side of the detector, the detector receives light transmitted through the balloon and around the stent struts. The stent appears dark in color and the balloon appears light in color. The contrast between the light and dark color in both embodiments can be used for edge analysis. Edge analysis comprises determining the edges of the stent and finding the center-line of stent surface to be coated. The edges and center-line determine the coating coordinates which are collected for each surface of the stent to be coated in the coating coordinates table.

In one non-limiting embodiment, the pre-scan is compared to an index of patterns in the processing unit. This can be used to confirm the accuracy of the edge analysis and provide a safety measure for detection of defects in the stent or errors in the edge analysis.

Figure 14:
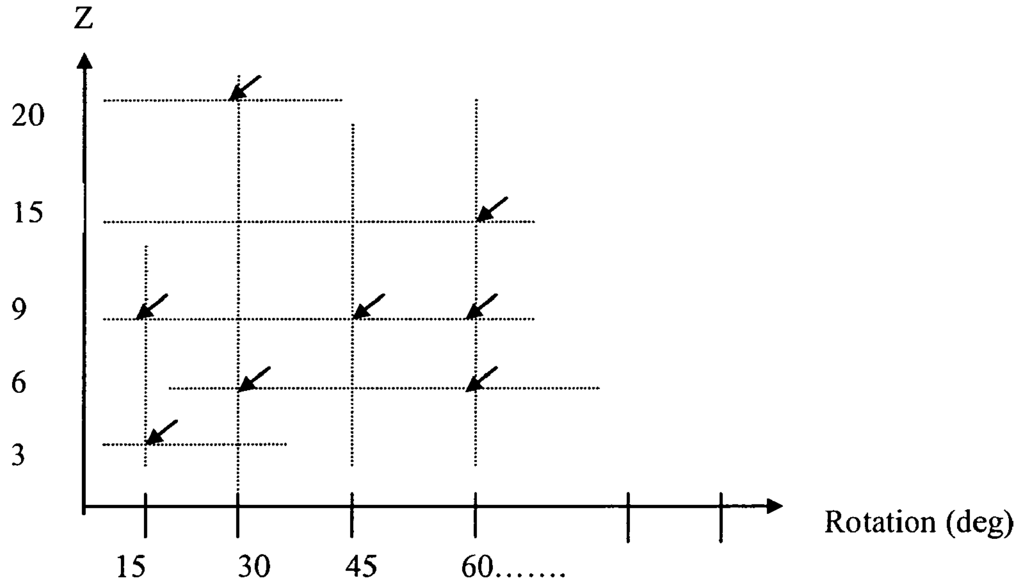
FIG. 14 is a mapping of coordinates where coating is applied as a function of distance along the divice and the relative axial rotation.

Coating coordinates can be interpreted and coded as raster or vector type of data forms. These data forms describe different translation of the applicator by the Z driver. Both data forms comprise using an algorithm to find all the coordinates of the stent that should be coated and compiling a map of "to be coated points" or coordinates. FIG. 14 illustrates a map of coordinates showing the point location on Z,R as a function of the relative axial rotation R in degrees or radians.

Vector type coating comprises taking the unique variables (e.g., Z and rotation), and using another algorithm to select the shortest distance or otherwise most efficient path to move between one coating coordinate and the next most proximate coordinate to be coated. Vector coating can also comprise creating a list of coordinates in sequential order. Table 1 illustrates a "best pass algorithm" as a coordinate table correlating location on Z to angle of rotation for each coordinate.

TABLE 1

| Coordinate no. | Z | Rotation |
|---|---|---|
| 1 | 3 | 15 |
| 2 | 6 | 30 |
| 3 | 9 | 45 |
| 4 | 6 | 60 |
| 5 | 9 | 60 |
| 6 | 15 | 60 |

Control software in the processing unit can calculate a set of movement vectors for the application control module between each set of sequential coordinates. Vector parameters may comprise coordinates, Δz (change in location between two adjacent points or coordinates on Z axis), Δrot (change in angle between coordinates), velocity between the coordinates, etc. Table 2 illustrates vectors that can be calculated from coordinate table in Table 1. Each vector can have a different velocity associated with it represented as values a, b, and c. Each vector can have a difference quantity associated with it represented as values d, e, f, g, h which may be the same of different. Other parameters can also be associated with each vector.

TABLE 2

| Vector | Δz | Δrot | Velocity | Quantity |
|---|---|---|---|---|
| 1–2 | 3 | 15 | a | d |
| 2–3 | 3 | 15 | a | e |
| 3–4 | −3 | 15 | a | f |
| 4–5 | 3 | 0 | b | g |
| 5–6 | 6 | 0 | c | h |

A raster type coating comprises using an algorithm to find all the coordinates of the stent that should be coated and compiling a map of coordinates. This is similar to vector type coating as is illustrated in FIG. 14. Raster type coating, however, also comprises taking the unique variables (e.g., Z and rotation), and using a different algorithm to calculate and compile a coordinate table of Z coordinates for each rotation angle in predetermined increments of rotation. The term "rotation resolution" refers to the number of increments in rotation angle. Raster type coating is rotation-resolution-specific. This means that raster printing is calculated and executed at one specific rotation resolution, or in a variety of other manipulations inter-relating the prosthetic item to be coated, the holder for such prosthetic and the applicator nozzle. Table 3 illustrates a coordinate table correlating angle of rotation with locations on Z. These locations: Z1, Z2, Z3, Z4, etc. represent intersections with the surface of the stent to be coated at each angle of rotation.

TABLE 3

| ROTATION ANGLE | Z1 | Z2 | Z3 | Z4 |
|---|---|---|---|---|
| 15 | 3 | 9 | | |
| 30 | 6 | 20 | | |
| 45 | 9 | | | |
| 60 | 6 | 9 | 15 | |

Control software in the processing unit can calculate the Z coordinates for each angular position and direct the application control module and coating applicator to go to an angular rotation position and move along Z at a regulated, constant or variable velocity. While moving along Z, the coating applicator injects at Z1, Z2, Z3, Z4, etc. After traveling the full length of the stent along Z, the application control module moves the coating applicator to the next angle of rotation, changes the direction along Z (now opposite the previous direction) which the coating applicator travels. While traveling in this new direction, the coating applicator injects over the next Z locations.

Additional raster-based manipulations could include, for example, rotational movements of the stent in conjunction with serial, stepped Z-axis movements, or "screw-like" movements along a helical path of the stent accomplished by simultaneous movement of rotation and stepped Z-axis movements as is described below. In any event, the raster-based coating process results in motion with respect to the stent and applicator which covers the entire prosthetic, while the vector-based coating process only travels over the "to be coated" surfaces. Consequently, the vector-based approach is object dependent, while the raster-based approach is simply system defined.

Figure 11:
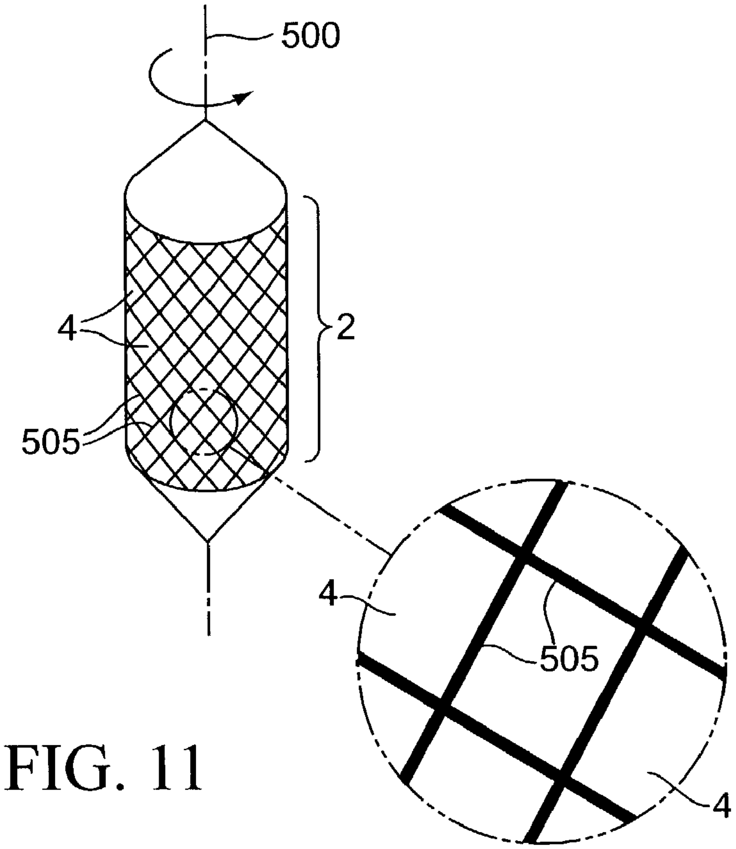
FIG. 11 illustrates a detail of a stent on a balloon catheter, and a blowup perspective of the stent surface to be coated.

FIG. 11 illustrates a stent 2 on a balloon catheter 4. The axis of rotation, Z, is also the axis of symmetry 500 for the stent. The magnified window of FIG. 11 shows the stent structure to be coated 505 and gaps in stent structure where balloon catheter 4 is not covered by the stent. During scanning, the stent is rotated in incremental angles according to the rotation resolution to generate the coordinate table. During coating, the application control module rotates the stent in the same incremental angles and positions the coating applicator at the Z locations to coat the stent. In one non-limiting embodiment, the coating applicator can drop-on-demand a coating with accuracy as is known in the art of ink-jet printing.

Figure 9A:
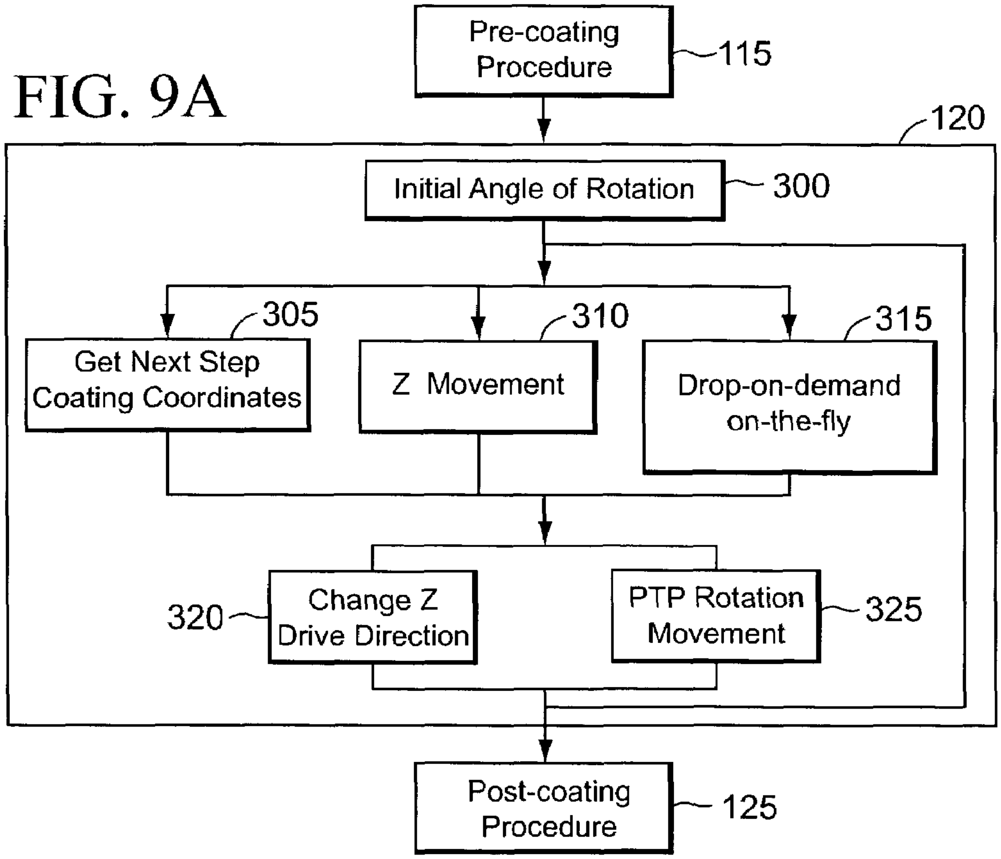
FIG. 9A is a flow chart of a non-limiting embodiment of the coating procedure according to the present invention.

The flowchart of FIG. 9A illustrates an embodiment of the coating procedure 120. The present embodiment contemplates raster coating accomplished by longitudinal movement of the applicator along the length of a cylindrical body and point-to-point ("PTP") rotation of the cylindrical body or applicator around the circumference of the cylindrical body. An initial angle of rotation is selected 300. The application control module moves the coating applicator along the Z axis 310, while controlling drop-on-demand at Z coordinate 315, and receiving the next coating coordinate from the processing unit 305. Once the coating applicator has moved along the length of the stent, the application control module changes the direction of travel along the Z axis of the coating applicator 320, and rotates the stent to the next angle of rotation 325. This process is repeated by repeating steps 310–325 until the stent has been coated according to the coordinate table. In one non-limiting embodiment, the change in incremental angle of rotation can be one-half of one degree and can require up to 500 rotations of the stent to coat each point in the coordinate table. Multiple coatings can be applied sequentially or simultaneously by repeating the steps and/or changing the coating reservoir.

In another embodiment, raster coating can be accomplished by coating along the circumferential rotation of the cylindrical body or applicator with PTP longitudinal movement of the applicator along the length of the cylindrical body. In another embodiment, raster coating can be accomplished by both circumferential rotation of the cylindrical body or applicator and longitudinal movement of the applicator with PTP longitudinal movement of the applicator or PTP rotation of the cylindrical body or applicator along the circumference of the cylindrical body. This embodiment results in a spiral or "screw" predetermined path.

In other embodiments, raster coating can be accomplished by following a predetermined path to apply coating material at desired locations of the prosthesis without regard to the pattern of the coating. In some embodiments, this predetermined path can incorporate the overall contour or geometrical shape of the prosthesis to efficiently cover the surface area which includes the desired locations to be coated. In some certain embodiments, efficiency can be realized by utilizing axes of symmetry or other geometrical simplifications of the overall contour of the prosthesis.

Figure 9B:
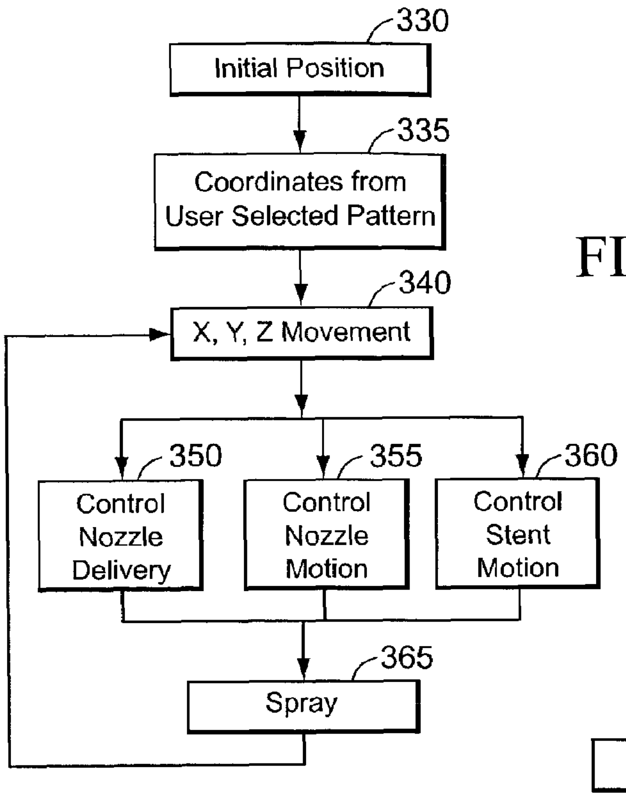
FIG. 9B is a flow chart of a procedure for coating a stent using a pre-selected library.

The flowchart of FIG. 9B illustrates the coating procedure 155 which is known in the art. The coating nozzle is in an initial position 330. The controller receives coordinates from a user selected pattern 335. The controller interprets the coordinates into X, Y, and Z constant velocity movement 340, and positions the nozzle to jet by controlling the nozzle delivery 350, the nozzle motion 355, and/or the stent motion 360. The nozzle then drop-on-demand 365. Then the nozzle travels over the stent to the next coordinate based on the user selected patter.

Figure 9C:
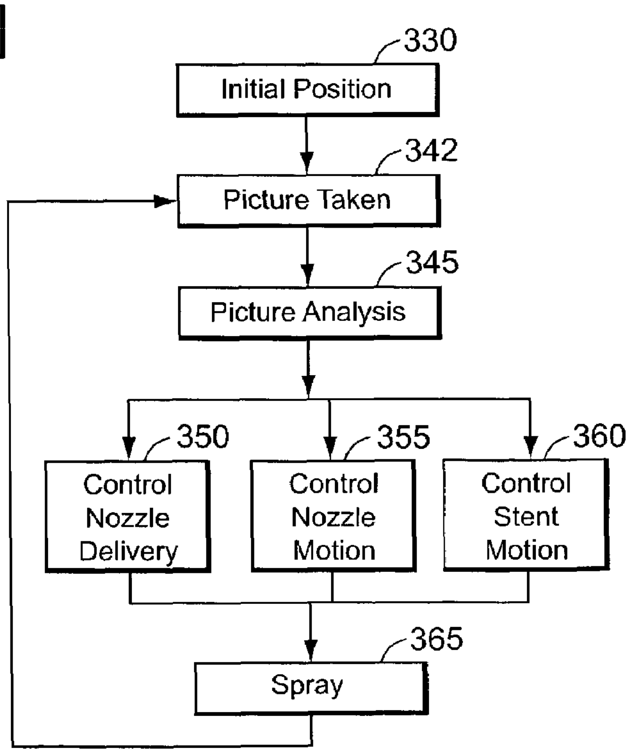
FIG. 9C is a flow chart of a procedure for coating a stent using real-time imaging.

The flowchart of FIG. 9C illustrates the coating procedure 155 which is known in the art also begins with the coating nozzle at an initial position 330. A picture of the nozzle, stent, and/or coating is taken 342. The picture is analyzed using vision software 345. The controller interprets the picture and positions the nozzle to jet by controlling the nozzle delivery 350, the nozzle motion 355, and/or the stent motion 360. The nozzle then drop-on-demand 365. This requires real-time imaging and adjustment prior to coating portions of the stent.

Figure 10:
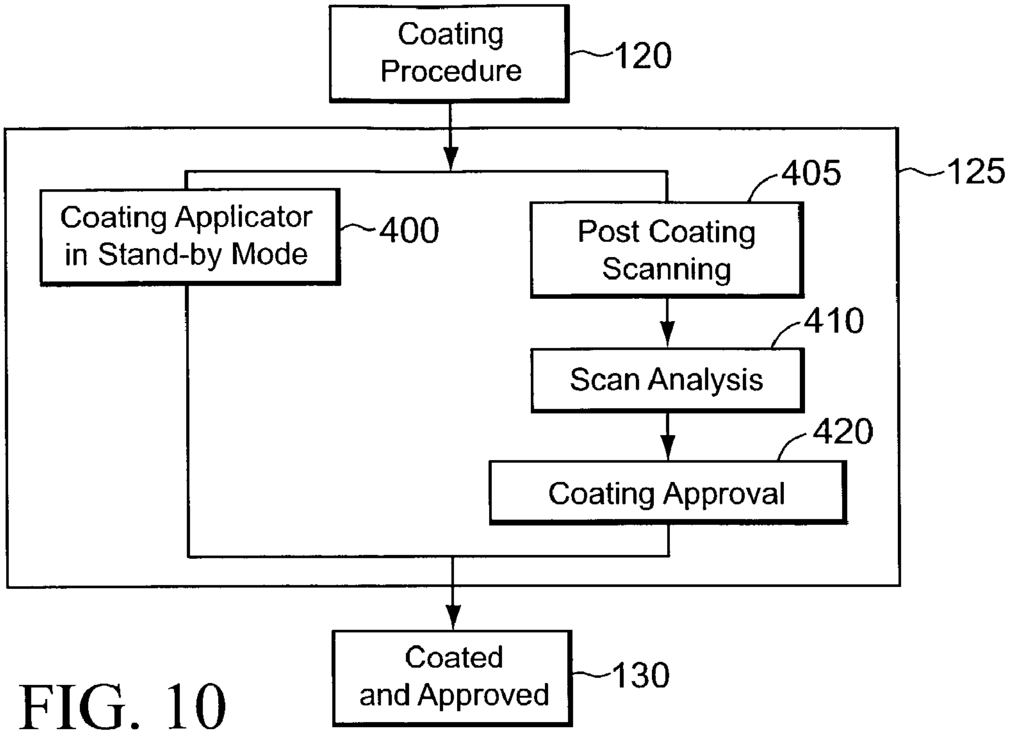
FIG. 10 is a flow chart of a non-limiting embodiment of the post-coating procedure according to the present invention.

The flowchart in FIG. 10 illustrates an embodiment of the present invention including a post-coating procedure 125. The coating applicator is held in stand-by mode 400, while the stent is post-scanned 405, scan analysis 410 analyzes the coated stent for mistakes in coating and provides coating quality assurance and approval 420. If approved, the stent coating is complete 130. In one non-limiting embodiment, the coating comprises pigment to facilitate scan analysis by differentiating between the stent and coating. In one non-limiting embodiment, the pre-scan images can be used for the approval of the stent. Post-scanning facilitates locating coordinates where coating was not applied because of jetting problems. Post-scanning also facilitates in locating leakage or "overspray" points where the coating has leaked from the stent onto the balloon catheter.

Figure 12:
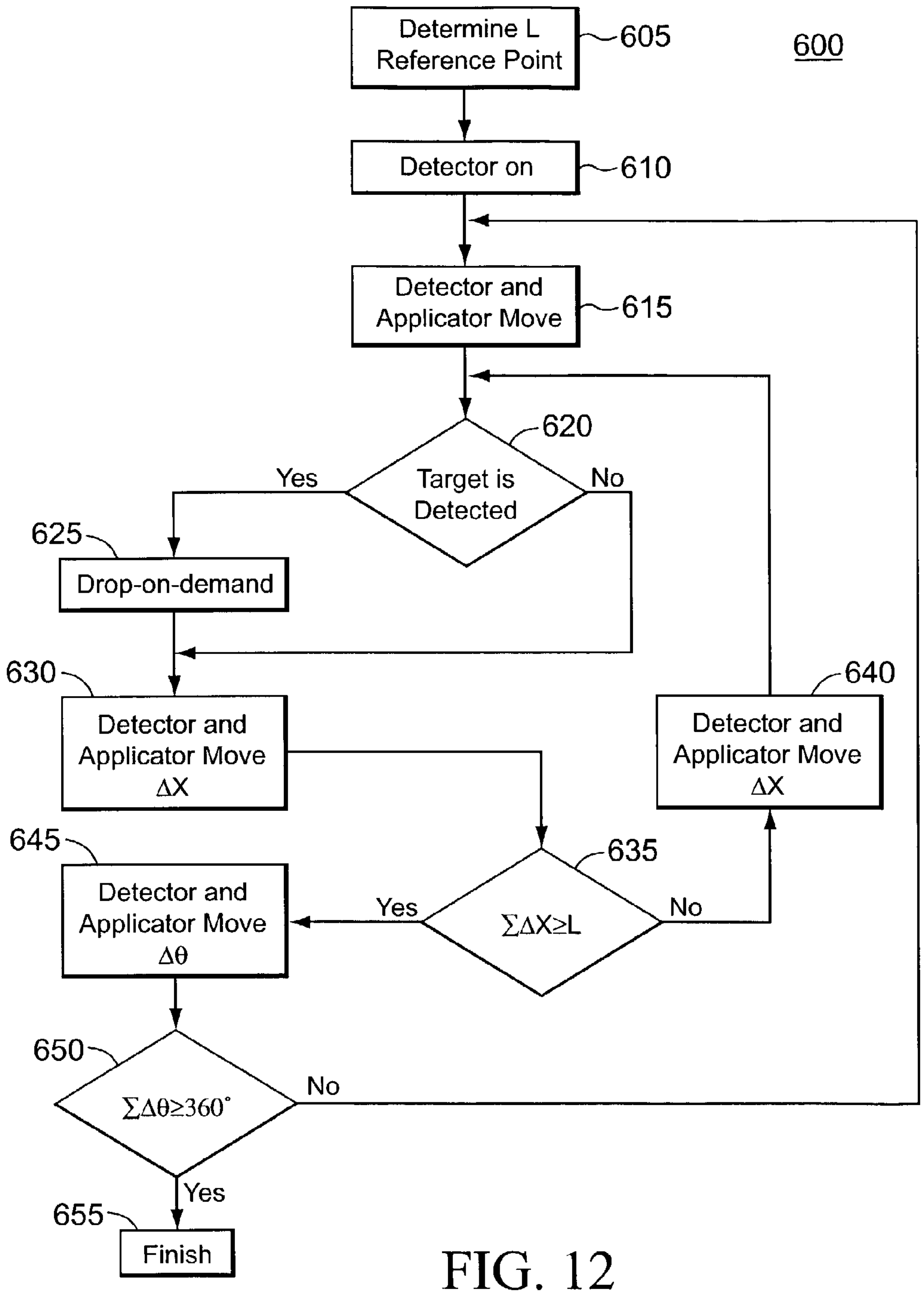
FIG. 12 illustrates a flow chart of a non-limiting embodiment of raster coating without the use of pre-scanning or post-scanning.
Figure 13:
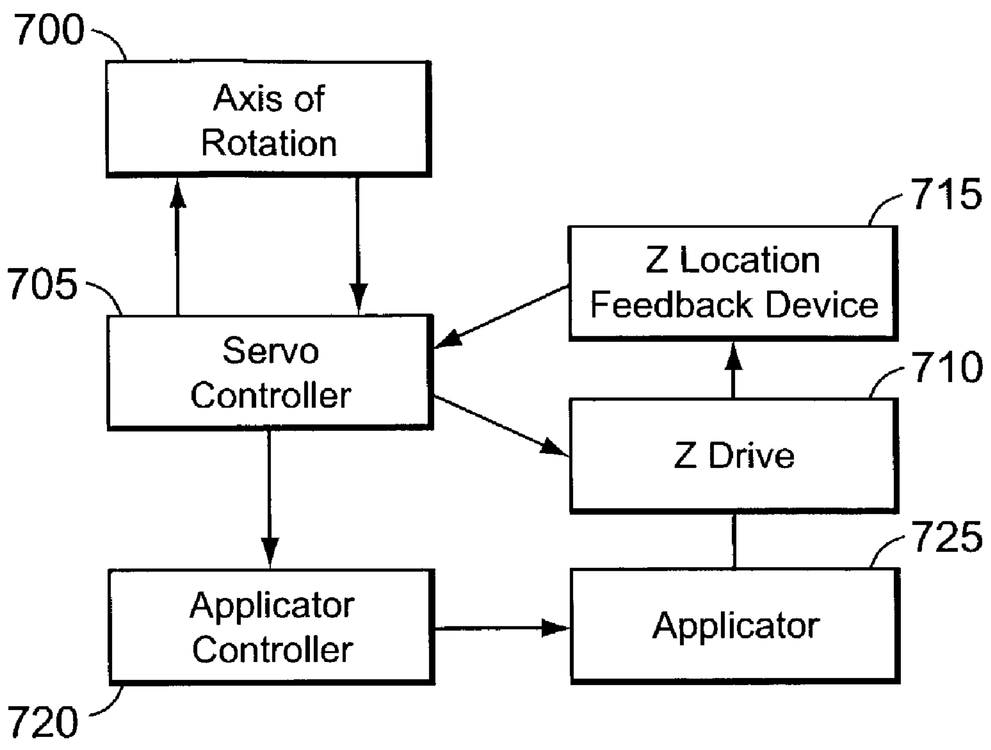
FIG. 13 illustrates a flow chart of an embodiment of "on-the-fly" translation of the applicator and delivery of the coating material. In alternative embodiments, the servo controller 705, Z drive 710, and Z location feedback device 715 can be all be bundled into the application controller 720.

The flow chart in FIG. 12 illustrates an embodiment of raster coating without pre-scanning or post-scanning. The method for coating a prosthesis 600, begins with setting 605 the predetermined length L, incremental linear movement $\Delta x$, and incremental angular movement $\Delta\theta$, along with a reference point recognized as a characteristic feature of the prosthesis. The detector is turned on 610. The detector and applicator move 615 linearly from the reference point an incremental distance $\Delta x$ and $\Delta\theta$ along L. The detector looks for targets 620 as desired locations on the prosthesis to be coated. If the detector finds a target, the applicator drop-on-demand 625. If the detector does not find a target or after the applicator drop-on-demand 625, the detector and applicator move $\Delta x$ 630. The detector determines whether it has traveled the full L of the prosthesis 635 by determining whether the sum of the $\Delta x$ movements is greater than or equal to L ($\Sigma\Delta x \geqq L$). If the detector has not traveled the full L, then the detector and applicator move $\Delta x$ 640 and look for a target 620. If the detector has traveled the full L, then the detector and applicator move $\Delta\theta$ 645. The detector determined whether it has traveled around the entire contour of the prosthesis 650 by determining whether the sum of the $\Delta\theta$ movements is greater than or equal to 360 degrees ($\Sigma\Delta\theta \geqq 360°$). If the detector has not traveled 360 degrees, then the detector and applicator move 615 linearly an incremental distance $\Delta x$ and $\Delta\theta$ along L. If the detector has traveled 360 degrees, then the coating is finished 655.

The present invention teaches a method for coating a prosthesis as well as an apparatus for coating a prosthesis, a system for coating a prosthesis, and an application control module for coating a prosthesis.

It will be appreciated that the above descriptions are intended only to serve as examples, and that many other embodiments are possible within the spirit and the scope of the present invention.

What is claimed is:

1. A method for applying a coating material, the method comprising:
- providing a prosthesis having a pattern of identifiable features;
- pre-scanning substantially an entire surface area of said prosthesis, prior to applying the coating material, to identify said identifiable features and to obtain coating coordinates for said identified features; and
- applying the coating material to a surface of the prosthesis at substantially each of said coating coordinates by moving a coating material applicator relative to the prosthesis,
- wherein the movement of the coating material applicator relative to the prosthesis does not substantially follow along any portion of the pattern of identifiable features.

2. A method according to claim 1, further comprising:
- post-scanning said prosthesis after applying the coating material.

3. A method according to claim 2, wherein said post-scanning comprises rotating said prosthesis and detecting of said coated prosthesis.

4. A method according to claim 1, wherein said pre-scanning comprises rotating said prosthesis and detecting of said prosthesis.

5. A method according to claim 4, wherein said detecting comprises detecting energy from said identifiable features of said prosthesis.

6. A method according to claim 5, wherein said pre-scanning further comprises analyzing images to identify edges associated with said prosthesis.

7. A method according to claim 6, wherein said pre-scanning further comprises determining said coating coordinates from said identified edges.

8. A method according to claim 4, wherein said detecting comprises optically distinguishing a first type of surface from a second type of surface.

9. A method according to claim 1, wherein said coating material is chosen from polymers, therapeutic agents, and mixtures thereof.

10. The method as recited in claim 1, wherein a path the applicator takes relative to the prosthesis comprises a substantially helical path around the prosthesis.

11. The method as recited in claim 1, wherein a path the application takes is a substantially linear path oriented substantially parallel to a longitudinal axis of the prosthesis, the method further comprising:

moving a coating material applicator along the predetermined path back and forth across the surface area of the prosthesis from a first end of the prosthesis to a second end of the prosthesis; and applying the coating material to the surface of the prosthesis at substantially each point on the predetermined path that corresponds to a coating coordinate.

12. The method as recited in claim 1, wherein a path the applicator takes relative to the prosthesis comprises a plurality of helical paths oriented substantially parallel to a longitudinal axis of the prosthesis, the method further comprising:

moving the coating material applicator and the prosthesis relative to one another such that the coating material applicator moves along each helical path across the surface area of the prosthesis from a first end of the prosthesis to a second end of the prosthesis; and applying the coating material to the surface of the prosthesis at substantially each point on each helical path that corresponds to a coating coordinate.

13. A method of applying a coating material to a prosthesis having a topological pattern, the method comprising:

scanning the topological pattern, prior to applying the coating material, to identify a plurality of coating locations at which the coating material is to be applied to the prosthesis;

calculating a plurality of coating coordinates as a function of the identified plurality of coating locations; and moving a coating material applicator and the prosthesis relative to one another to define a motion path of the coating material applicator with respect to the prosthesis and causing the coating material applicator to apply the coating material to the prosthesis at substantially each point on the motion path that corresponds to one of the coating coordinates, wherein the motion path does not substantially follow along the topological pattern.

14. The method as recited in claim 13, wherein the motion path does not substantially follow along any portion of the topological pattern.

15. The method as recited in claim 13, wherein:

the motion path is a substantially linear path oriented substantially parallel to a longitudinal axis of the prosthesis.

16. The method as recited in claim 13, further comprising:

moving the coating material applicator along a linear path oriented substantially parallel to a longitudinal axis of the prosthesis; and rotating the prosthesis about its longitudinal axis while moving the coating material applicator along the linear path, wherein the motion path comprises a helical path about the prosthesis.

17. The method as recited in claim 13, wherein the motion path is defined by:

moving the coating material applicator to a first point along the longitudinal length of the prosthesis; and rotating the prosthesis about its longitudinal axis while the coating material applicator is stationary at the first point, wherein the motion path describes a ring about the prosthesis.

18. The method as recited in claim 17, further comprising:

moving the coating material applicator to a second point along the longitudinal length of the prosthesis; and rotating the prosthesis about its longitudinal axis while the coating material applicator is stationary at the second point, wherein the motion path describes a plurality of longitudinally offset rings about the prosthesis.

19. The method as recited in claim 13, further comprising:

rotating the prosthesis about its longitudinal axis to a first angular position under the coating material applicator; and moving the coating material applicator along a substantially linear path oriented substantially parallel to a longitudinal axis of the prosthesis while the prosthesis is stationary at the first angular position, wherein the motion path describes a raster movement about the prosthesis.

20. The method as recited in claim 13, wherein scanning comprises:

generating an image of the topological pattern; and processing the generated image.

21. The method as recited in claim 20, wherein calculating comprises:

determining an angle of rotation component and a linear position location for each coating coordinate.

* * * * *